US012694960B1

(12) United States Patent
Wang et al.

(10) Patent No.: US 12,694,960 B1
(45) Date of Patent: Jul. 28, 2026

(54) METHODS AND SYSTEMS FOR GENERATING A DIAGNOSTIC REPORT

(71) Applicants: SHANGHAI UNITED IMAGING INTELLIGENCE CO., LTD., Shanghai (CN); HENAN PROVINCIAL PEOPLE'S HOSPITAL, Zhengzhou (CN)

(72) Inventors: Meiyun Wang, Zhengzhou (CN); Dinggang Shen, Shanghai (CN); Jianmin Yuan, Shanghai (CN); Tuoyu Cao, Shanghai (CN); Yaping Wu, Zhengzhou (CN); Yan Bai, Zhengzhou (CN); Wei Wei, Zhengzhou (CN); Nan Meng, Zhengzhou (CN)

(73) Assignees: SHANGHAI UNITED IMAGING INTELLIGENCE CO., LTD., Shanghai (CN); HENAN PROVINCIAL PEOPLE'S HOSPITAL, Zhengzhou (CN)

( * ) Notice: Subject to any disclaimer, the term of this patent is extended or adjusted under 35 U.S.C. 154(b) by 0 days.

(21) Appl. No.: 19/437,251

(22) Filed: Dec. 30, 2025

(30) Foreign Application Priority Data

Dec. 22, 2025 (CN) .......................... 202511946704.2
Dec. 26, 2025 (CN) .......................... 202512003510.5

(51) Int. Cl.
*G16H 15/00* (2018.01)
*G06T 7/00* (2017.01)
(Continued)

(52) U.S. Cl.
CPC ........... *G16H 15/00* (2018.01); *G06T 7/0012* (2013.01); *G16H 30/40* (2018.01);
(Continued)

(58) Field of Classification Search
CPC ........ G16H 15/00; G16H 30/40; G16H 20/00; G16H 50/20; G16H 30/20; G06T 7/0012;
(Continued)

(56) References Cited

U.S. PATENT DOCUMENTS 6,138,045 A * 10/2000 Kupinski .................. G06T 7/11
378/62
2004/0264749 A1 * 12/2004 Skladnev ............. A61B 5/0059
382/128
(Continued)

FOREIGN PATENT DOCUMENTS

CN 110379492 A 10/2019
CN 111105872 A 5/2020
(Continued)

OTHER PUBLICATIONS

Chang; Shaojie et al. "Exploring Dual-Energy CT Spectral Information for Machine Learning-Driven Lesion Diagnosis in Pre-Log Domain" Jan. 2023, IEEE (Year: 2023).*
(Continued)

*Primary Examiner* — John Villecco
*Assistant Examiner* — Alejandro Hernandez
(74) *Attorney, Agent, or Firm* — Poseidon Advanced IP LLC

(57) ABSTRACT

Provided are a method and a system for generating a diagnostic report. The method includes: obtaining raw scanning data of a target object, a reconstructed image of the target object, and clinical information of the target object; determining first lesion information of the target object and second lesion information of the target object based on the raw scanning data and the reconstructed image; determining whether the target object includes a lesion based on the first lesion information and the second lesion information; in response to determining that the target object includes the
(Continued)

lesion, generating a target reconstructed image of the lesion using a simulation scanning model; obtaining third lesion information by performing feature extraction on the target reconstructed image; generating a structured diagnostic report using a report generation model based on the first lesion information, the second lesion information, the third lesion information, and the clinical information.

20 Claims, 10 Drawing Sheets

(51) Int. Cl.
  *G16H 20/00*   (2018.01)
  *G16H 30/40*   (2018.01)
(52) U.S. Cl.
  CPC ............... *G06T 2207/20081* (2013.01); *G06T 2207/30096* (2013.01); *G16H 20/00* (2018.01)
(58) Field of Classification Search
  CPC . G06T 2207/20081; G06T 2207/30096; G06T 11/003; G06T 11/008; A61B 5/00; G06V 10/70
  See application file for complete search history.

(56)      References Cited

U.S. PATENT DOCUMENTS

| | | | | |
|---|---|---|---|---|
| 2006/0247525 | A1* | 11/2006 | Huo ...................... | G06T 7/0012 |
| | | | | 600/437 |
| 2018/0315182 | A1* | 11/2018 | Rapaka ................ | G06T 7/0012 |
| 2019/0159744 | A1* | 5/2019 | Mensah ................ | G16H 50/30 |
| 2020/0008772 | A1 | 1/2020 | Ghamari | |
| 2022/0180516 | A1* | 6/2022 | Mavroeidis .............. | G06T 7/11 |
| 2022/0192619 | A1 | 6/2022 | Sun | |
| 2023/0022921 | A1* | 1/2023 | Lim ....................... | G06N 20/00 |
| 2023/0360794 | A1 | 11/2023 | Lyu | |
| 2024/0242835 | A1* | 7/2024 | Giltnane ............... | G06T 7/0012 |
| 2024/0290449 | A1* | 8/2024 | Roh ....................... | G16H 50/20 |
| 2025/0037823 | A1* | 1/2025 | Erbach ................... | G16H 10/60 |
| 2025/0111503 | A1* | 4/2025 | Peng ......................... | G06T 7/11 |
| 2025/0174001 | A1* | 5/2025 | Peng ...................... | G16H 30/40 |
| 2026/0004937 | A1* | 1/2026 | Schaap .................. | G16H 50/30 |

FOREIGN PATENT DOCUMENTS

| | | | | | |
|---|---|---|---|---|---|
| CN | 112435554 A | | 3/2021 | | |
| CN | 111353940 B | | 4/2021 | | |
| CN | 114022360 A | | 2/2022 | | |
| CN | 114549503 A | | 5/2022 | | |
| CN | 112966580 B | | 7/2022 | | |
| CN | 114926339 B | | 2/2023 | | |
| CN | 116344001 A | * | 6/2023 | ............ | G16H 30/20 |
| CN | 119361089 A | | 1/2025 | | |
| CN | 119850771 A | | 4/2025 | | |
| CN | 120072176 A | | 5/2025 | | |
| CN | 120241111 A | | 7/2025 | | |
| CN | 120599256 A | | 9/2025 | | |
| CN | 120746947 A | | 10/2025 | | |
| CN | 120807675 A | | 10/2025 | | |
| KR | 20260021881 A | * | 2/2026 | ............... | G06T 7/60 |

OTHER PUBLICATIONS

First Office Action in Chinese Application No. 202511946704.2 mailed on Jan. 23, 2026, 12 pages.

* cited by examiner

100

Figure 2:
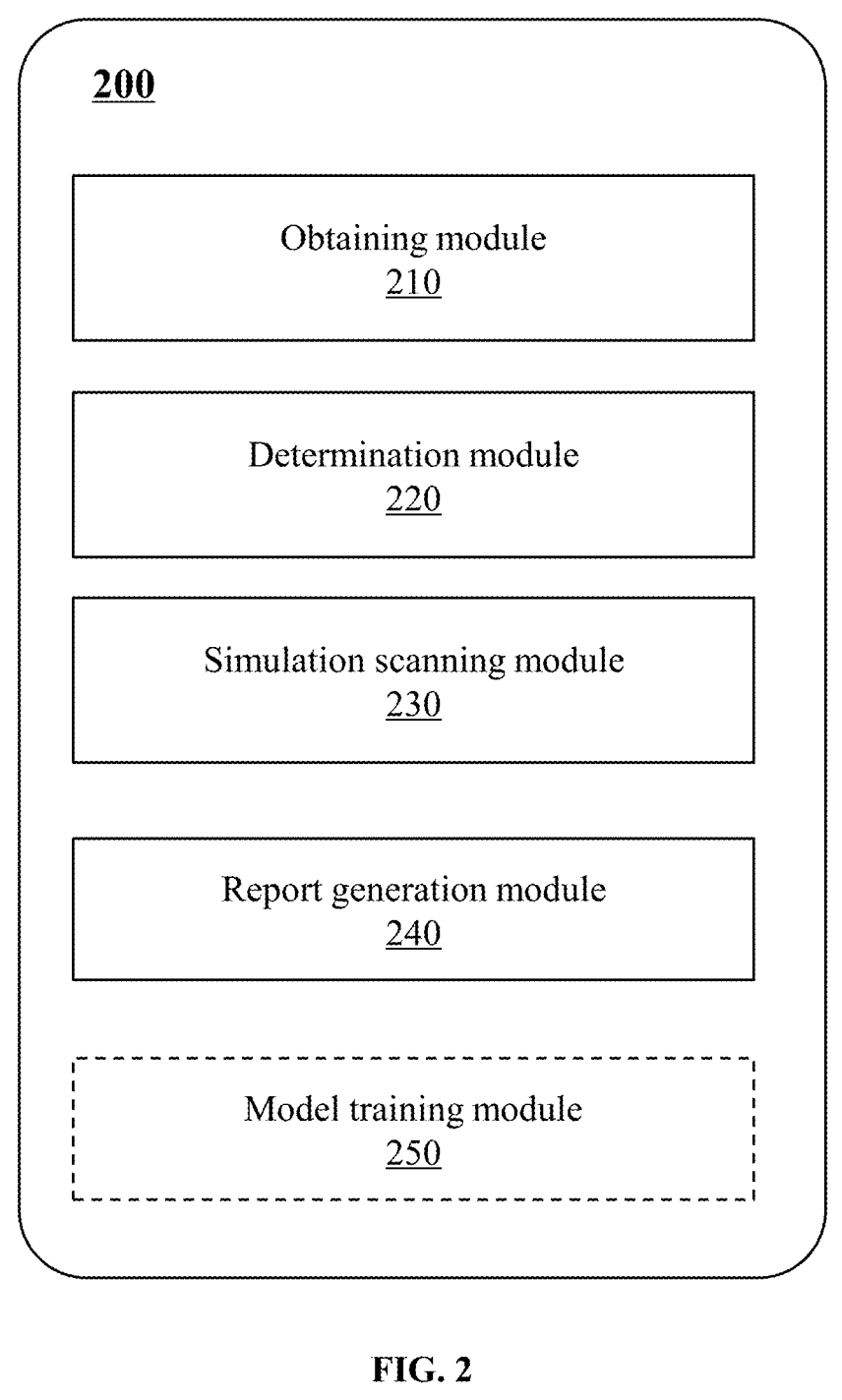

200

Obtaining module
210

Determination module
220

Simulation scanning module
230

Report generation module
240

Model training module
250

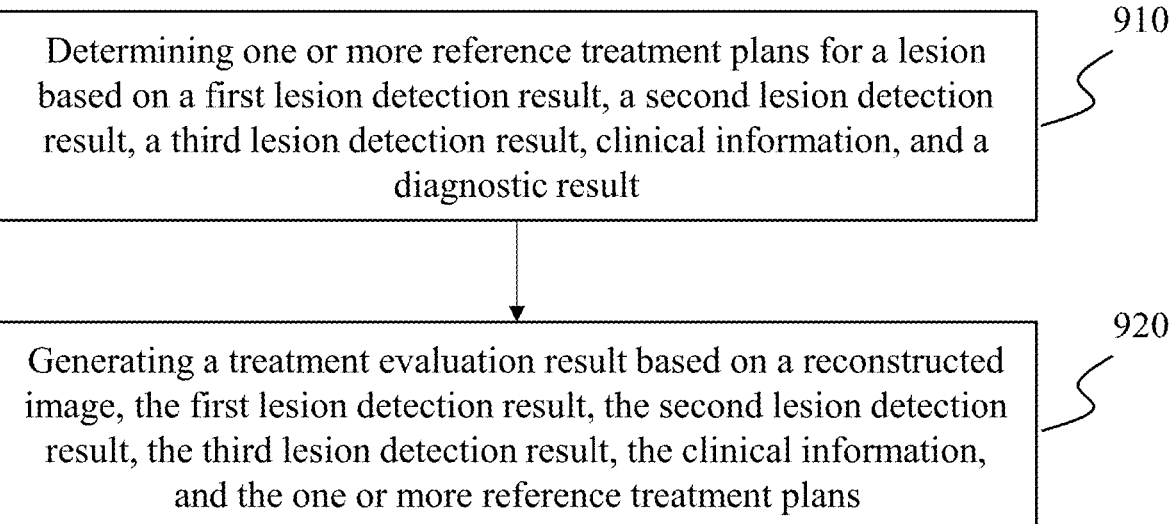

910

Determining one or more reference treatment plans for a lesion based on a first lesion detection result, a second lesion detection result, a third lesion detection result, clinical information, and a diagnostic result

920

Generating a treatment evaluation result based on a reconstructed image, the first lesion detection result, the second lesion detection result, the third lesion detection result, the clinical information, and the one or more reference treatment plans

FIG. 9

METHODS AND SYSTEMS FOR GENERATING A DIAGNOSTIC REPORT

CROSS-REFERENCE TO RELATED APPLICATIONS

This application claims priority to the Chinese Patent Application No. 202512003510.5, filed on Dec. 26, 2025, and claims priority to the Chinese Patent Application No. 202511946704.2, filed on Dec. 22, 2025, the contents of each of which are hereby incorporated by reference.

TECHNICAL FIELD

The present disclosure relates to the field of medical technology, and in particular, to methods and systems for generating diagnostic reports.

BACKGROUND

The current conventional diagnostic procedure for a patient is as follows: a physician issues an examination order, the patient undergoes a scan; subsequently, raw data from the scan is used to reconstruct a reconstructed medical image. The reconstructed medical image is then reviewed sequentially by a radiologist and a clinical physician to determine whether an additional scan targeting the lesion (e.g., a high-resolution scan or a contrast-enhanced scan) is necessary. If it is determined that the additional scan targeting the lesion is necessary, the clinical physician then issues another examination order, followed by the additional scan. This constitutes a sequential, labor-intensive process that leads to a prolonged diagnostic and treatment cycle and low efficiency.

Furthermore, clinical physicians primarily rely on a single reconstructed image for diagnosis, which provides limited informational dimensions. This may lead to an incomplete assessment of the lesion, consequently posing two risks: first, missed or incorrect diagnoses; and second, defensive and unnecessary additional scans performed to clarify the diagnosis, which increases the patient's radiation exposure, economic cost, and time cost.

Therefore, an efficient and accurate method and system for generating a diagnostic report are provided.

SUMMARY

In a first aspect of the present disclosure, a method for generating a diagnostic report is provided. The method may include: obtaining raw scanning data of a target object, a reconstructed image of the target object, and clinical information of the target object, wherein the raw scanning data is obtained by scanning the target object using a medical imaging device, and the reconstructed image is generated based on the raw scanning data; determining, based on the raw scanning data, first lesion information of the target object; determining, based on the reconstructed image and the first lesion information, second lesion information of the target object; determining whether the target object includes a lesion based on the first lesion information and the second lesion information; in response to determining that the target object includes the lesion, generating, based on the raw scanning data and the reconstructed image, a target reconstructed image of the lesion using a simulation scanning model; obtaining third lesion information by performing feature extraction on the target reconstructed image; and generating a structured diagnostic report for the target object using a report generation model based on the first lesion information, the second lesion information, the third lesion information, and the clinical information.

In some embodiments, the first lesion information is determined by processing the raw scanning data using a raw data analysis model; the second lesion information is determined by processing the reconstructed image and the first lesion information using an image analysis model; and the third lesion information is determined by processing the target reconstructed image using a lesion analysis model. The raw data analysis model, the image analysis model, and the lesion analysis model are trained machine learning models.

In some embodiments, the raw data analysis model and the image analysis model are obtained by: obtaining sample raw data, a sample reconstructed image corresponding to the sample raw data, first label lesion information corresponding to the sample reconstructed image, and second label lesion information corresponding to the sample reconstructed image; obtaining the raw data analysis model by training a first preliminary model using the sample raw data and the first label lesion information; determining sample first lesion information corresponding to the sample raw data based on the sample raw data and the raw data analysis model; and obtaining the image analysis model by training a second preliminary model using the sample reconstructed image, the sample first lesion information, and the second label lesion information.

In some embodiments, in response to determining that historical diagnostic data relating to the lesion exists, the method further includes: determining lesion change information based on the historical diagnostic data, the first lesion information, the second lesion information, and the third lesion information; and generating the structured diagnostic report for the target object by processing the first lesion information, the second lesion information, the third lesion information, the clinical information, and the lesion change information using the report generation model.

In some embodiments, the simulation scanning model includes a simulation scanning module and an update module. The simulation scanning module is configured to generate an initial target reconstructed image based on the raw scanning data, the reconstructed image, the first lesion information, the second lesion information, and an initial scanning protocol parameter; and the update module is configured to generate the target reconstructed image based on the initial target reconstructed image.

In some embodiments, to generate the target reconstructed image based on the initial target reconstructed image, the update module is configured to: determine whether the initial target reconstructed image satisfies a preset condition; in response to determining that the initial target reconstructed image does not satisfy the preset condition, adjust the initial scanning protocol parameter to generate a target scanning protocol parameter; and generate the target reconstructed image based on the target scanning protocol parameter.

In some embodiments, the simulation scanning model is obtained by: obtaining a plurality of third training samples and a third preliminary model, each of the plurality of third training samples including sample raw data, a sample reconstructed image, sample first lesion information, sample second lesion information, a sample scanning protocol parameter, and a reference reconstructed image; and generating the simulation scanning model by training the third preliminary model using the plurality of third training samples based on a first loss function and a second loss function. During training, for each of the plurality of third training samples: a value of the first loss function is determined based on the reference reconstructed image and a predicted target reconstructed image generated by the third preliminary model; and a value of the second loss function is determined based on predicted raw scanning data and the sample raw data, the predicted raw scanning data being determined based on the predicted target reconstructed image.

In some embodiments, the first lesion information includes a first lesion detection result and a first confidence map, the second lesion information includes a second lesion detection result and a second confidence map, the third lesion information includes a third lesion detection result and a third confidence map, and the generating a structured diagnostic report for the target object using a report generation model based on the first lesion information, the second lesion information, the third lesion information, and the clinical information includes: determining a first weight corresponding to the first lesion detection result, a second weight corresponding to the second lesion detection result, and a third weight corresponding to the third lesion detection result based on the clinical information, the first confidence map, the second confidence map, and the third confidence map; and generating the structured diagnostic report for the target object by processing the first lesion detection result, the second lesion detection result, the third lesion detection result, the first weight, the second weight, and the third weight using the report generation model.

In some embodiments, the determining a first weight corresponding to the first lesion detection result, a second weight corresponding to the second lesion detection result, and a third weight corresponding to the third lesion detection result based on the clinical information, the first confidence map, the second confidence map, and the third confidence map includes: determining a case type of the target object based on the clinical information; determining a preset first weight corresponding to the first lesion detection result, a preset second weight corresponding to the second lesion detection result, and a preset third weight corresponding to the third lesion detection result based on the case type; and determining the first weight, the second weight, and the third weight by adjusting the preset first weight, the preset second weight, and the preset third weight based on the first confidence map, the second confidence map, and the third confidence map.

In some embodiments, the structured diagnostic report for the target object includes a diagnostic result and a traceability basis, and the traceability basis indicates information on which the diagnostic result is based.

In some embodiments, the report generation model includes a feature fusion module and a structured report generation module. The feature fusion module is configured to determine a consistency detection result, fused feature information, and an initial traceability basis corresponding to the fused feature information by performing consistency detection and feature fusion based on the first lesion detection result, the second lesion detection result, the third lesion detection result, the first weight, the second weight, the third weight, and the clinical information. The structured report generation module is configured to: determine the diagnostic result based on the fused feature information; determine the traceability basis based on the initial traceability basis; and generate the structured diagnostic report based on the consistency detection result, the diagnostic result, and the traceability basis.

In some embodiments, the structured diagnostic report for the target object further includes a treatment evaluation result, and the report generation model further includes a treatment prediction module. The treatment prediction module is configured to: determine one or more reference treatment plans for the lesion based on the first lesion detection result, the second lesion detection result, the third lesion detection result, the clinical information, and the diagnostic result; and generate the treatment evaluation result based on the reconstructed image, the first lesion detection result, the second lesion detection result, the third lesion detection result, the clinical information, and the one or more reference treatment plans. The structured report generation module is further configured to generate the structured diagnostic report based on the treatment evaluation result, the consistency detection result, the diagnostic result, and the traceability basis.

In some embodiments, the treatment evaluation result includes, for each reference treatment plan of the one or more reference treatment plans, at least one of an efficacy prediction indicator, a predicted medical image of the lesion, a side effect assessment, and a recommendation index.

In some embodiments, determining one or more reference treatment plans for the lesion based on the first lesion detection result, the second lesion detection result, the third lesion detection result, the clinical information, and the diagnostic result includes: constructing a target optimization problem based on the first lesion detection result, the second lesion detection result, the third lesion detection result, the clinical information, and the diagnostic result, the target optimization problem including a first optimization objective, a second optimization objective, a third optimization objective, and a fourth optimization objective, where the first optimization objective is quantified by a first objective function for characterizing efficacy, the second optimization objective is quantified by a second objective function for characterizing safety, the third optimization objective is quantified by a third objective function for characterizing treatment cost, and the fourth optimization objective is quantified by a fourth objective function for characterizing compliance with treatment guidelines; and generating the one or more reference treatment plans by solving, under a medical constraint, the target optimization problem using an optimization algorithm based on the first optimization objective, the second optimization objective, the third optimization objective, and the fourth optimization objective.

In some embodiments, the generating the one or more reference treatment plans by solving, under a medical constraint, the target optimization problem using an optimization algorithm based on the first optimization objective, the second optimization objective, the third optimization objective, and the fourth optimization objective includes: obtaining a value preference of the target object; for each optimization objective of the first optimization objective, the second optimization objective, the third optimization objective, and the fourth optimization objective, determining an optimization weight corresponding to the optimization objective based on the value preference; generating the one or more reference treatment plans by solving, under the medical constraint, the target optimization problem using the optimization algorithm based on the first optimization objective, the second optimization objective, the third optimization objective, the fourth optimization objective, and the optimization weight corresponding to each optimization objective.

In a second aspect of the present disclosure, a system for generating a diagnostic report is provided. The system may include at least one storage device configured to store computer instructions; and at least one processor in communication with the at least one storage device. When executing the computer instructions, the at least one processor is configured to cause the system to perform operations including: obtain raw scanning data of a target object, a reconstructed image of the target object, and clinical information of the target object, where the raw scanning data is obtained by scanning the target object using a medical imaging device, and the reconstructed image is generated based on the raw scanning data; determine, based on the raw scanning data, first lesion information of the target object; determine, based on the reconstructed image and the first lesion information, second lesion information of the target object; determine whether the target object includes a lesion based on the first lesion information and the second lesion information; in response to determining that the target object includes the lesion, generate, based on the raw scanning data and the reconstructed image, a target reconstructed image of the lesion using a simulation scanning model; obtain third lesion information by performing feature extraction on the target reconstructed image; and generate a structured diagnostic report for the target object using a report generation model based on the first lesion information, the second lesion information, the third lesion information, and the clinical information.

In a third aspect of the present disclosure, a non-transitory computer-readable storage medium is provided. The storage medium stores at least one set of instructions, and when one or more processors of a computing device execute the at least one set of instructions, the at least one set of instructions causes the computing device to perform a method. The method includes: obtaining raw scanning data of a target object, a reconstructed image of the target object, and clinical information of the target object, wherein the raw scanning data is obtained by scanning the target object using a medical imaging device, and the reconstructed image is generated based on the raw scanning data; determining, based on the raw scanning data, first lesion information of the target object; determining, based on the reconstructed image and the first lesion information, second lesion information of the target object; determining whether the target object includes a lesion based on the first lesion information and the second lesion information; in response to determining that the target object includes the lesion, generating, based on the raw scanning data and the reconstructed image, a target reconstructed image of the lesion using a simulation scanning model; obtaining third lesion information by performing feature extraction on the target reconstructed image; and generating a structured diagnostic report for the target object using a report generation model based on the first lesion information, the second lesion information, the third lesion information, and the clinical information.

Additional aspects of the present disclosure may be set forth in the following description. Through studying the following description and corresponding drawings, or through understanding of the production or operation of embodiments, additional aspects of the present disclosure will become apparent to the skilled in the art. The features of the present disclosure may be realized and obtained by practicing or using aspects of the methods, means, and combinations set forth in the detailed examples below.

BRIEF DESCRIPTION OF THE DRAWINGS

The present disclosure will be further illustrated by way of exemplary embodiments, which will be described in detail through the accompanying drawings. These embodiments are not limiting, and in these embodiments, the same numbering denotes the same structure.

FIG. 2 is a schematic diagram illustrating an exemplary system for generating a diagnostic report according to some embodiments of the present disclosure;

FIG. 9 is a schematic diagram illustrating an exemplary process for generating a reference treatment plan according to some embodiments of the present disclosure.

DETAILED DESCRIPTION

Figure 1:
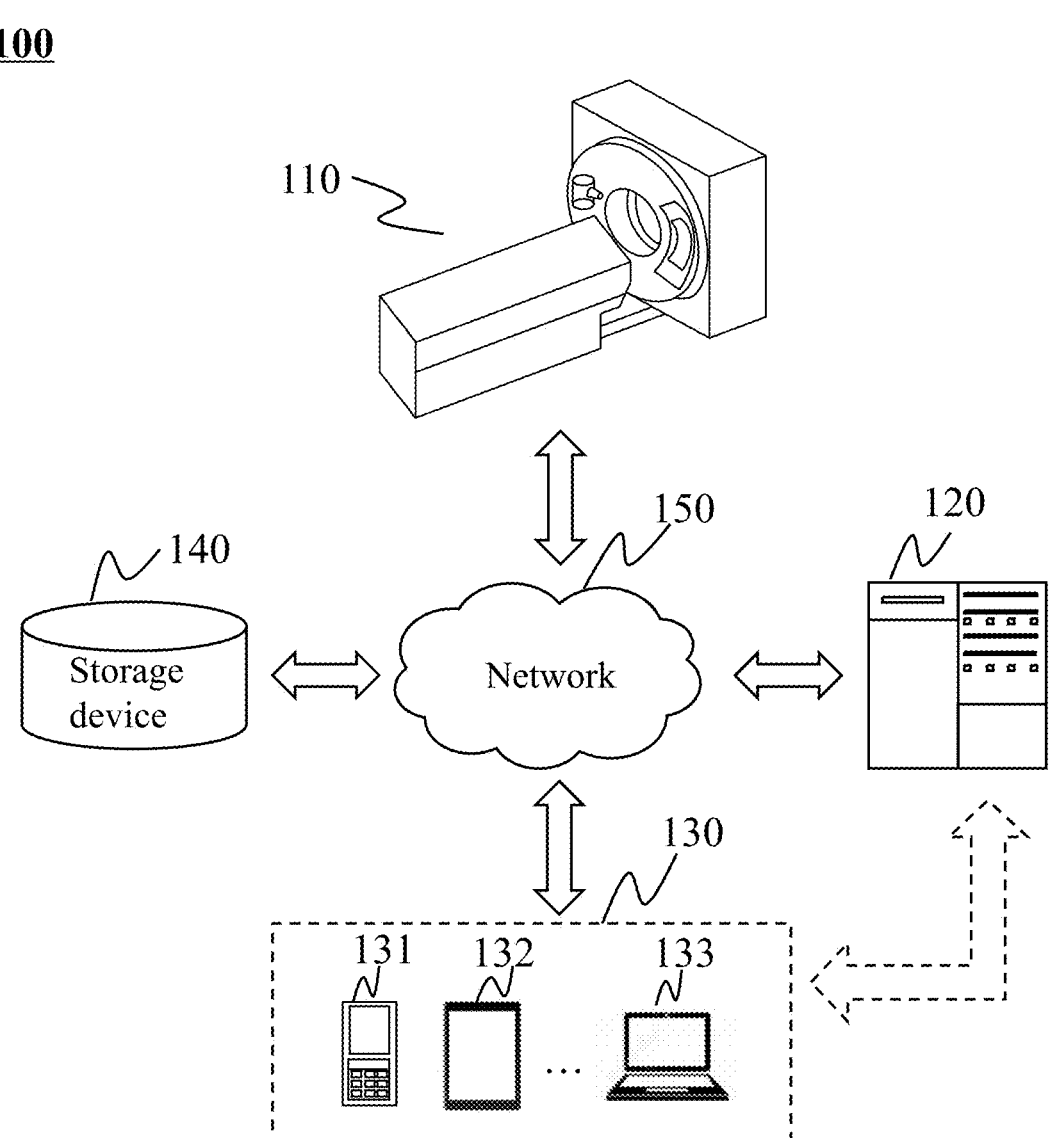
FIG. 1 is a schematic diagram illustrating an exemplary application scenario of a system for generating a diagnostic report according to some embodiments of the present disclosure.

In order to illustrate the technical solutions of the embodiments of the present disclosure more clearly, the accompanying drawings required for describing the embodiments are briefly introduced below. Obviously, drawings described below are only some examples or embodiments of the present disclosure. Those skilled in the art, without further creative efforts, may apply the present disclosure to other similar scenarios according to these drawings. It should be understood that the purposes of these illustrated embodiments are only provided to those skilled in the art to practice the application, and not intended to limit the scope of the present disclosure. Unless obviously obtained from the context or the context illustrates otherwise, the same numeral in the drawings refers to the same structure or operation.

It will be understood that the term "system," "device," "unit," and/or "module" used herein are one method to distinguish different components, elements, parts, sections or assemblies of different levels in ascending order. However, the terms may be displaced by another expression if they achieve the same purpose.

The terminology used herein is for the purpose of describing particular example embodiments only and is not intended to be limiting. As used herein, the singular forms "a," "an," and "the" may be intended to include the plural forms as well, unless the context clearly indicates otherwise.

It will be further understood that the terms "comprise," "comprises," and/or "comprising," "include," "includes," and/or "including," when used in the present disclosure, specify the presence of stated operations and/or elements, but do not preclude the presence or addition of one or more other operations and/or elements thereof.

The flowcharts used in the present disclosure illustrate operations that systems implement according to some embodiments of the present disclosure. It is to be expressly understood, the operations of the flowcharts may be implemented not in order. Conversely, the operations may be implemented in an inverted order, or simultaneously. Moreover, one or more other operations may be added to the flowcharts. One or more operations may be removed from the flowcharts.

FIG. 1 is a schematic diagram illustrating an exemplary application scenario of a system for generating a diagnostic report according to some embodiments of the present disclosure. As shown in FIG. 1, an application scenario 100 of the system for generating a diagnostic report may include a medical imaging device 110, a processing device 120, a terminal device 130, a storage device 140, and a network 150. In some embodiments, the processing device 120 may be part of the medical imaging device 110. Connections among components in the application scenario 100 may be variable. As shown in FIG. 1, the medical imaging device 110 may be connected to the processing device 120 via the network 150. For example, the medical imaging device 110 may be directly connected to the processing device 120. As another example, the storage device 140 may be directly connected to the processing device 120 or connected via the network 150. As a further example, the terminal device 130 may be directly connected to the processing device 120 (as indicated by the dashed arrow connecting the terminal device 130 and the processing device 120), or may be connected to the processing device 120 via the network 150.

The medical imaging device 110 may be a non-invasive scanning imaging device for disease diagnosis or research purposes. In some embodiments, the medical imaging device 110 may scan an object within a detection region or a scanning region to obtain raw scanning data of the object. In some embodiments, the medical imaging device 110 may include a single-modality scanner and/or a multi-modality scanner. The single-modality scanner may include an ultrasound scanner, an X-ray scanner, a computed tomography (CT) scanner, a magnetic resonance imaging (MRI) scanner, a positron emission tomography (PET) scanner, an optical coherence tomography (OCT) scanner, an ultrasound (US) scanner, an intravascular ultrasound (IVUS) scanner, or any combination thereof. The multi-modality scanner may include an X-ray-MRI scanner, a PET-X-ray scanner, a single-photon emission computed tomography-magnetic resonance imaging (SPECT-MRI) scanner, a positron emission tomography-computed tomography (PET-CT) scanner, a digital subtraction angiography-magnetic resonance imaging (DSA-MRI) scanner, or the like. In some embodiments, the processing device 120 may be integrated on the medical imaging device 110, or the medical imaging device 110 and the processing device 120 may be implemented by the same entity to realize functions of the medical imaging device 110. The medical imaging device 110 provided above is for illustrative purposes only and is not intended to limit the scope of the present disclosure.

The processing device 120 may process data and/or information obtained from the medical imaging device 110, the terminal device 130, the storage device 140, or other components of the application scenario 100. For example, the processing device 120 may obtain raw scanning data of a target object and generate a reconstructed image of the target object based on the raw scanning data. The processing device 120 may determine first lesion information of the target object based on the raw scanning data, and then determine second lesion information of the target object based on the reconstructed image and the first lesion information. Furthermore, the processing device 120 may determine whether the target object includes a lesion based on the first lesion information and the second lesion information. In response to determining that the target object includes the lesion, the processing device 120 may generate a target reconstructed image of the lesion using a simulation scanning model based on the raw scanning data and the reconstructed image, and obtain third lesion information by performing feature extraction on the target reconstructed image. Then, the processing device 120 may generate a structured diagnostic report for the target object using a report generation model based on the first lesion information, the second lesion information, the third lesion information, and the clinical information.

In some embodiments, the processing device 120 may be local or remote. For example, the processing device 120 may access information and/or data from the medical imaging device 110, the terminal device 130, and/or the storage device 140 via the network 150.

The terminal device 130 may include a mobile device 131, a tablet computer 132, a laptop computer 133, or any combination thereof. In some embodiments, the terminal device 130 may be part of the processing device 120.

The storage device 140 may store data, instructions, and/or any other information. In some embodiments, the storage device 140 may store data obtained from the medical imaging device 110, the processing device 120, and/or the terminal device 130, e.g., the raw scanning data obtained by the medical imaging device 110.

The network 150 may include any suitable network capable of facilitating information and/or data exchange. In some embodiments, at least one component of the application scenario 100 (e.g., the medical imaging device 110, the processing device 120, the terminal device 130, and the storage device 140) may exchange information and/or data with at least one other component in the application scenario 100 via the network 150. For example, the processing device 120 may obtain the raw scanning data of the target object from the medical imaging device 110 via the network 150. As another example, the terminal device 130 may obtain the structured diagnostic report for the target object from the processing device 120 via the network 150.

It should be noted that the application scenario 100 is provided merely for illustrative purposes and is not intended to limit the scope of the present disclosure. For those skilled in the art, various modifications or variations may be made based on the description of the present disclosure. For example, the application scenario 100 may further include an input device and/or an output device. As another example, the application scenario 100 may realize similar or different functions on other devices. However, such variations and modifications will not depart from the scope of the present disclosure.

FIG. 2 is a schematic diagram illustrating an exemplary system for generating a diagnostic report according to some embodiments of the present disclosure.

As shown in FIG. 2, in some embodiments, a system 200 for generating a diagnostic report may include an obtaining module 210, a determination module 220, a simulation scanning module 230, and a report generation module 240.

In some embodiments, the system 200 for generating a diagnostic report may further include a model training module 250. In some embodiments, functions corresponding to the system 200 for generating a diagnostic report may be executed by the processing device 120. For example, the obtaining module 210, the determination module 220, the simulation scanning module 230, the report generation module 240, and the model training module 250 may be modules within the processing device 120.

The obtaining module 210 may be configured to obtain raw scanning data of a target object, a reconstructed image of the target object, and clinical information of the target object. The raw scanning data is obtained by scanning the target object using a medical imaging device, and the reconstructed image is generated based on the raw scanning data. More descriptions regarding obtaining raw scanning data of the target object, the reconstructed image of the target object, and the clinical information of the target object may be found elsewhere in the present disclosure, e.g., operation 310 of FIG. 3 and related descriptions thereof.

The determination module 220 may be configured to determine, based on the raw scanning data, first lesion information of the target object. More descriptions regarding determining first lesion information of the target object based on the raw scanning data may be found elsewhere in the present disclosure, e.g., operation 320 of FIG. 3 and related descriptions thereof.

The determination module 220 may be configured to determine, based on the reconstructed image and the first lesion information, second lesion information of the target object. More descriptions regarding determining the second lesion information of the target object based on the reconstructed image and the first lesion information may be found elsewhere in the present disclosure, e.g., operation 330 of FIG. 3 and related descriptions thereof.

The determination module 220 may be further configured to determine whether the target object includes a lesion based on the first lesion information and the second lesion information. More descriptions regarding determining whether the target object includes a lesion based on the first lesion information and the second lesion information may be found elsewhere in the present disclosure, e.g., operation 340 of FIG. 3 and related descriptions thereof.

The simulation scanning module 230 may be configured to: in response to determining that the target object includes the lesion, generate, based on the raw scanning data and the reconstructed image, a target reconstructed image of the lesion using a simulation scanning model. More descriptions regarding generating the target reconstructed image of the lesion using the simulation scanning model based on the raw scanning data and the reconstructed image, may be found elsewhere in the present disclosure, e.g., operation 350 of FIG. 3 and related descriptions thereof.

The determination module 220 may be further configured to obtain third lesion information by performing feature extraction on the target reconstructed image. More descriptions regarding obtaining third lesion information by performing feature extraction on the target reconstructed image may be found elsewhere in the present disclosure, e.g., operation 360 of FIG. 3 and related descriptions thereof.

The report generation module 240 may be configured to generate a structured diagnostic report for the target object using a report generation model based on the first lesion information, the second lesion information, the third lesion information, and the clinical information. More descriptions regarding generating the structured diagnostic report for the target object using the report generation model may be found elsewhere in the present disclosure, e.g., operation 370 of FIG. 3 and related descriptions thereof.

It should be understood that the system 200 and the modules of the system 200 shown in FIG. 2 may be implemented in various ways. For example, in some embodiments, the system 200 and the modules thereof may be implemented with hardware, software, or a combination of software and hardware.

It should be noted that the descriptions of the system and the modules of the system 200 above are provided merely for convenience of description and as illustrations, and should not limit the present disclosure to the scope of the exemplified embodiments. It should be understood that for those skilled in the art, after understanding the principles of the system, various modules may be arbitrarily combined, or subsystems may be constituted to connect with other modules without departing from these principles. For example, in some embodiments, the modules disclosed in FIG. 2 may be different modules within one system, or one module may implement the functions of two or more of the above-mentioned modules. For example, the various modules may share a storage module, or each module may have its own respective storage module. In some embodiments, the model training module 250 and other modules may be implemented by different systems. For example, the model training module 250 may be implemented by a computing device of a supplier of the machine learning models, while the other modules may be implemented by a computing device of a user of the machine learning models. Such modifications or the like all fall within the scope of the present disclosure.

Figure 3:
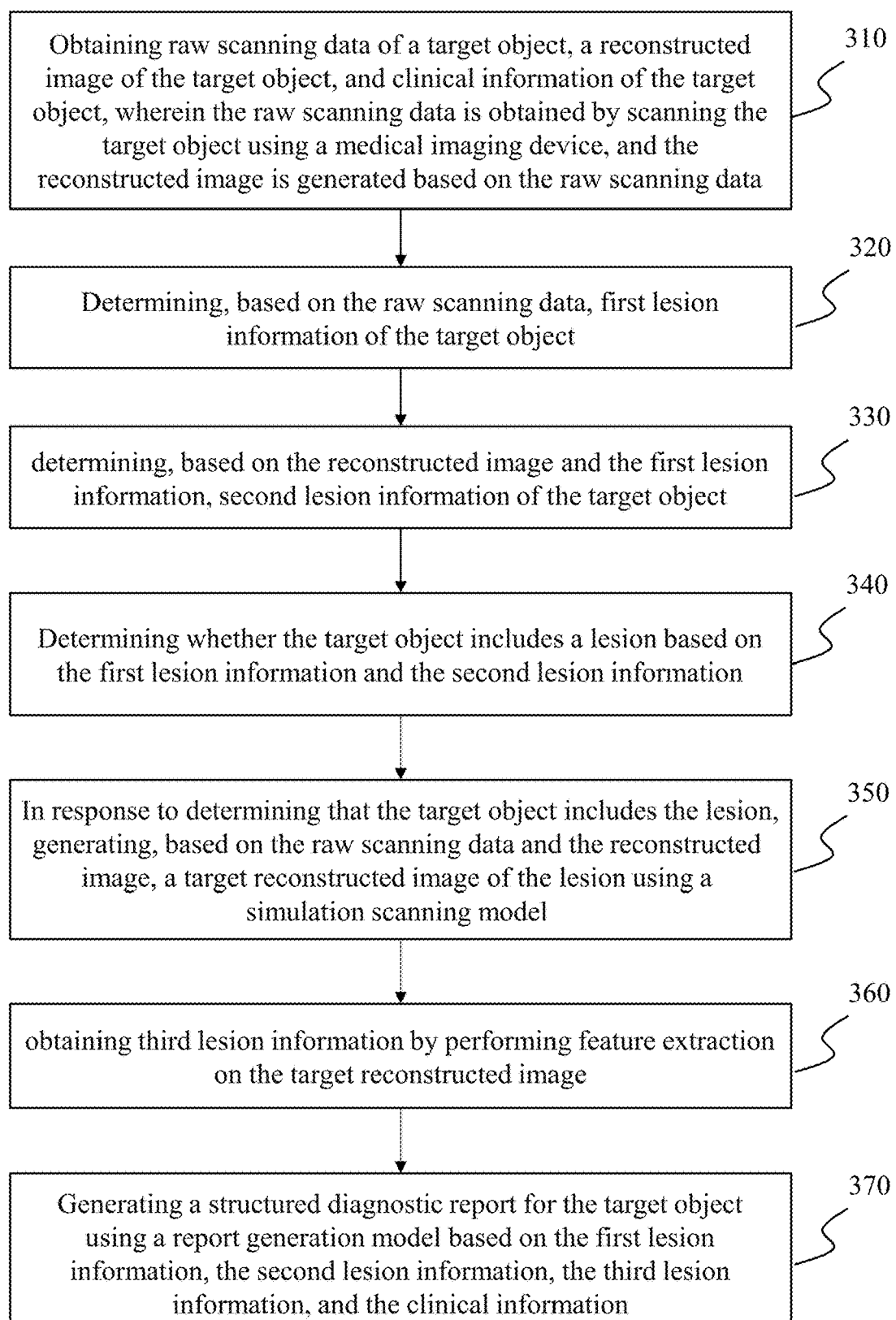
FIG. 3 is a schematic diagram illustrating an exemplary process for generating a structured diagnostic report according to some embodiments of the present disclosure.

FIG. 3 is a schematic diagram illustrating an exemplary process for generating a structured diagnostic report according to some embodiments of the present disclosure. In some embodiments, one or more operations of the process 300 may be implemented in the application scenario 100 shown in FIG. 1 or performed by the system 200 for generating a diagnostic report shown in FIG. 2. For example, the process 300 may be performed by modules of the processing device 120. As shown in FIG. 3, the process 300 may include the following operations.

In 310, raw scanning data of a target object, a reconstructed image of the target object, and clinical information of the target object may be obtained. The raw scanning data is obtained by scanning the target object using a medical imaging device, and the reconstructed image is generated based on the raw scanning data. In some embodiments, operation 310 may be performed by the processing device 120 or the obtaining module 210.

The target object refers to an object that needs to undergo a medical scan. The target object may include the whole or a part of a biological object and/or a non-biological object involved in the scanning process. The following description uses a human body as an example.

The raw scanning data refers to original data obtained by scanning the target object using the medical imaging device 110. For example, when an MRI scanner is used to scan the target object, the raw scanning data may include k-space data. As another example, when a CT scanner is used to scan the target object, the raw scanning data may include projection data or sinogram data. As yet another example, when a PET scanner is used to scan the target object, the raw scanning data may include coincidence event data. In some embodiments, the processing device 120 may obtain the raw scanning data directly from the medical imaging device 110. In some embodiments, the raw scanning data may be generated in advance and stored in a storage device (e.g., the storage device 140 or an external storage device), and the processing device 120 may obtain the raw scanning data from that storage device.

The reconstructed image refers to a medical image including anatomical structure information of the target object. Merely by way of example, the reconstructed image may include a CT image, an MRI image, a PET image, or the like. In some embodiments, the processing device 120 may use various reconstruction algorithms to reconstruct the raw scanning data to generate the reconstructed image. For example, for CT scans, the reconstruction algorithms may include an analytical reconstruction algorithm, an iterative reconstruction algorithm, etc. As another example, for MRI scans, the reconstruction algorithms may include a two-dimensional/three-dimensional Fourier transform algorithm, a compressed sensing reconstruction algorithm, a deep learning or artificial intelligence-based reconstruction algorithm. As yet another example, for PET scans, the reconstruction algorithms may include the analytical reconstruction algorithm (e.g., Filtered Back Projection (FBP)), the iterative reconstruction algorithm, or the like. The iterative reconstruction algorithms may include a Maximum-Likelihood Expectation-Maximization (MLEM) algorithm, a point spread function modeling-based iterative reconstruction algorithm, a deep learning-based PET reconstruction algorithm, or the like.

In some embodiments, the processing device 120 may generate the reconstructed image based on the raw scanning data and a confidence corresponding to the raw scanning data (e.g., a first confidence map in operation 320). Regions with high confidences are preserved and enhanced, while regions with low confidences (e.g., noise or artifacts) are suppressed or interpolated, thereby significantly improving the quality of the reconstructed image.

The clinical information of the target object may include basic information of the target object, current symptom information, medical history, a preliminary diagnosis result by a physician, or the like. The basic information includes age, gender, height, weight, occupation, living environment, etc. The medical history includes historical diagnosed disease information, historical surgery information, historical trauma information, etc. The processing device 120 may obtain the clinical information of the target object from a medical information system of a hospital.

In 320, based on the raw scanning data, first lesion information of the target object may be determined. In some embodiments, operation 320 may be performed by the processing device 120 or the determination module 220.

The first lesion information refers to information related to lesions of the target object and determined based on the raw scanning data. The first lesion information may include a first lesion detection result. The first lesion detection result may include whether a lesion exists, a count of lesion(s), a severity of the lesion (also referred to as a lesion severity), and a type of the lesion (also referred to as a lesion type, e.g., solid tumor, cyst, or hemorrhage). The severity of the lesion refers to a probability that the lesion is benign or malignant. A lower probability of the lesion being benign indicates a higher severity of the lesion, and a higher probability of the lesion being benign indicates a lower severity of the lesion. A lower probability of the lesion being malignant indicates a lower severity of the lesion, and a higher probability of the lesion being malignant indicates a higher severity of the lesion. In some embodiments, the first lesion detection result further includes a size of the lesion (also referred to as a lesion size) and a position of the lesion (also referred to as a lesion position). For example, if the raw scanning data is projection data, the first lesion detection result includes the lesion position in a projection domain.

In some embodiments, the first lesion information further includes a first confidence map. The first confidence map includes a confidence of each data point in the raw scanning data. The confidence of each data point may be in a range of 0 to 1. A higher score of the confidence of the data point indicates a higher confidence for the data point, that is, a signal from the data point is more likely to originate from an anatomical structure of the target object and less likely to originate from noise or artifacts.

In some embodiments, the first lesion information is determined by processing the raw scanning data using a raw data analysis model. The raw data analysis model is a trained machine learning model. The raw data analysis model refers to a model that determines lesion information based on raw scanning data. In some embodiments, the processing device 120 may input the raw scanning data into the raw data analysis model, and the raw data analysis model may output the first lesion information. In some embodiments, the raw scanning data may be preprocessed to obtain preprocessed raw scanning data, and the preprocessed raw scanning data is input into the raw data analysis model for processing. Exemplary preprocessing operations may include noise filtering, artifact correction and compensation, standardization, normalization, or the like.

In some embodiments, the raw data analysis model may include a machine learning model based on a convolutional neural network (CNN) and/or a Transformer model. For example, the raw data analysis model may include a Vision Transformer (ViT) model, a Swin Transformer model, a deep convolutional network model, etc. In some embodiments, the raw data analysis model includes a feature extraction module, a lesion detection module, and a confidence map prediction module. The lesion detection module and the confidence map prediction module are respectively connected to the feature extraction module to receive feature information output by the feature extraction module in parallel. The feature extraction module is configured to perform feature extraction on the input raw scanning data. In some embodiments, the feature extraction module includes a CNN unit and a Transformer encoder. The CNN unit is configured to extract multi-scale local feature maps from the raw scanning data. The Transformer encoder models global dependencies between local features output by the CNN unit using a self-attention mechanism. The lesion detection module detects lesions of the target object based on the feature information output by the feature extraction module and outputs the first lesion detection result. The confidence map prediction module is configured to predict the reliability (i.e., confidence) of each raw data point based on the feature information output by the feature extraction module and output the first confidence map. In some embodiments, the lesion detection module includes an anchor-based object detection module or an anchor-free object detection module. The confidence map prediction module includes a fully convolutional decoder, which is configured to upsample the feature information to the same spatial dimensions as the raw scanning data.

In some embodiments, the processing device 120 may obtain the raw data analysis model from one or more components (e.g., the storage device 140 or the terminal device 130) of the application scenario 100 of the system for generating a diagnostic report or from an external source via a network (e.g., the network 150). For example, the raw data analysis model is trained in advance by a computing device (e.g., the processing device 120) and stored in a storage device (e.g., the storage device 140). The processing device 120 may access the storage device to obtain the raw data analysis model.

Merely by way of example, the processing device 120 may obtain a plurality of first training samples. Each of the plurality of first training samples may include sample raw data of a sample object and first label lesion information. The first label lesion information serves as a label or gold standard for model training. Similar to the first lesion information, the first label lesion information includes a first label lesion detection result. The first label lesion detection result may include whether a lesion exists, a count of lesion(s), a size of the lesion, a severity of the lesion, and a type of the lesion (e.g., solid tumor, cyst, or hemorrhage). In some embodiments, the first label lesion detection result further includes a position of the lesion. In some embodiments, the first label lesion information further includes a first label confidence map. In some embodiments, the first label lesion information may be obtained based on a reconstructed image of the sample raw data. In some embodiments, the processing device 120 may obtain the first label lesion information by performing feature extraction on the reconstructed image of the sample raw data. In response to determining that the first label lesion detection result includes the position of the lesion, the processing device 120 may project the position of the lesion in an image domain to a raw data domain (e.g., the projection domain) via coordinate transformation to generate a position of the lesion in the raw data domain, and designate the position of the lesion in the raw data domain as the position of the lesion in the first label lesion detection result. In some embodiments, at least a portion of the first label lesion information may be confirmed manually by a user. For example, the count of the lesion(s) and the type of the lesion in the first label lesion information may be manually confirmed by the user.

Furthermore, the processing device 120 may obtain the raw data analysis model by training a first preliminary model based on the plurality of first training samples. The first preliminary model refers to an untrained machine learning model. The obtaining process and the structure of the first preliminary model are similar to those of the raw data analysis model and will not be elaborated here. During training, the sample raw data in the training samples may serve as model input of the first preliminary model, the first label lesion information corresponding to each of the plurality of first training samples may serve as a training label, and parameters of the first preliminary model may be iteratively updated until a termination condition is satisfied. Any suitable loss function (e.g., MSE) and any suitable optimizer (e.g., Adam optimizer) may be used to train the first preliminary model to obtain the raw data analysis model. In some embodiments, the raw data analysis model is obtained by sequentially or jointly training the first preliminary model and a second preliminary model. More descriptions may be found in FIG. 4 and related descriptions thereof.

The raw data analysis model may learn and identify information corresponding to weak, early-stage signals associated with specific lesions (e.g., tumors and hemorrhage). The information, which is often treated as noise or smoothed/weakened by filtering algorithms in standard image reconstruction processes, allows the capture of early abnormalities that are difficult to detect by traditional manners, thereby gaining valuable time for clinical intervention.

In 330, based on the reconstructed image and the first lesion information, second lesion information of the target object may be determined. In some embodiments, operation 330 may be performed by the processing device 120 or the determination module 220.

Similar to the first lesion information, the second lesion information refers to information related to lesions of the target object, and is determined based on the reconstructed image. The second lesion information includes a second lesion detection result. The second lesion detection result includes whether the lesion exists, the count of the lesion(s), the size of the lesion, the severity of the lesion, the type of the lesion (e.g., solid tumor, cyst, and hemorrhage), the position of the lesion, or the like. The position of the lesion in the second lesion detection result refers to a position in the image domain. In some embodiments, the second lesion detection result further includes anatomical structure information of each organ or tissue. For example, the anatomical structure information may include a position, a size, a density of each organ or tissue.

In some embodiments, the second lesion information further includes a second confidence map. The second confidence map includes a confidence of each pixel in the reconstructed image. The confidence of each pixel may be in a range of 0 to 1. A higher score of the confidence for the pixel indicates a higher confidence for the pixel, that is, the signal from the pixel is more likely to originate from the anatomical structure of the target object and less likely to originate from noise or artifacts.

In some embodiments, the second lesion information is determined by processing the reconstructed image and the first lesion information using an image analysis model. The image analysis model is a trained machine learning model. The image analysis model refers to a model that determines lesion information based on the reconstructed image and the first lesion information. In some embodiments, the processing device 120 may input the reconstructed image and the first lesion information into the image analysis model, and the image analysis model may output the second lesion information. In some embodiments, the processing device 120 may input only the reconstructed image into the image analysis model, and the image analysis model may output the second lesion information. In some embodiments, other manners may be employed to obtain the second lesion information. For example, the reconstructed image may be segmented using an image segmentation algorithm to obtain information (e.g., the position of the lesion, the type of the lesion, and the size of the lesion). The type of the lesion, the probability that the lesion is malignancy, etc., may be determined manually.

In some embodiments, the image analysis model may include a vision-language large model. For example, the image analysis model includes a visual encoder based on ViT or ResNet and a large language model (LLM) text decoder. The visual encoder is configured to analyze the anatomical structure, pathological features, and semantic information in the reconstructed image to extract visual features. The LLM text decoder is configured to autoregressively generate a text description based on the visual features. The visual encoder may include a Vision Transformer-based model, a convolutional neural network-based model, etc. The LLM text decoder may include an autoregressive language model, an encoder-decoder language model, etc.

In some embodiments, the processing device 120 obtains the image analysis model by a process similar to obtaining the raw data analysis model. Merely by way of example, the processing device 120 may obtain a plurality of second training samples. Each second training sample may include a sample reconstructed image of a sample object (which may also be referred to as a first sample reconstructed image), sample first lesion information, and second label lesion information. The second label lesion information serves as a label or gold standard for model training. The second label lesion information includes a second label lesion detection result. The second label lesion detection result includes whether the lesion exists, the count of the lesion(s), the size of the lesion, the severity of the lesion, the type of the lesion (e.g., solid tumor, cyst, and hemorrhage), the position of the lesion, or the like. In some embodiments, the second label lesion detection result further includes the anatomical structure information of each organ or tissue, e.g., the position, the size, and the density of each organ or tissue. In some embodiments, the second label lesion information further includes a second label confidence map. In some embodiments, the sample reconstructed image and the sample first lesion information are generated based on raw scanning data of the sample object. For example, the raw scanning data of the sample object may be reconstructed to generate the sample reconstructed image. The raw scanning data of the sample object may be input into the raw data analysis model to obtain the sample first lesion information. In some embodiments, the first label lesion information is obtained based on the reconstructed image of the sample raw data. In some embodiments, the processing device 120 may obtain the second label lesion information by performing feature extraction on the sample reconstructed image. In some embodiments, at least a portion of the second label lesion information may be confirmed manually by the user. For example, the count of the lesion(s), the type of the lesion in the second label lesion information may be manually confirmed by the user.

Furthermore, the processing device 120 may obtain the image analysis model by training a second preliminary model based on the plurality of second training samples. The second preliminary model refers to an untrained machine learning model. The obtaining process and the structure of the second preliminary model are similar to those of the image analysis model and will not be elaborated here. During training, the sample reconstructed image and the sample first lesion information in the second training samples may serve as model input of the second preliminary model, the second label lesion information corresponding to each second training sample may serve as a training label, and parameters of the second preliminary model may be iteratively updated until a termination condition is satisfied. Any suitable loss function (e.g., MSE) and any suitable optimizer (e.g., Adam optimizer) may be used to train the second preliminary model to obtain the image analysis model. In some embodiments, the image analysis model is obtained by sequentially or jointly training the first preliminary model and the second preliminary model. More descriptions may be found in FIG. 4 and related descriptions thereof.

In 340, whether the target object includes a lesion may be determined based on the first lesion information and the second lesion information. In some embodiments, operation 340 may be performed by the processing device 120 or the determination module 220.

In some embodiments, in response to determining that at least one of the first lesion information and the second lesion information indicates the presence of the lesion and/or the count of the lesion(s) being greater than or equal to 1, the processing device 120 determines that the target object includes the lesion. For example, in response to determining that the count of the lesion(s) in the first lesion detection result is greater than or equal to 1, the processing device 120 determines that the target object includes the lesion. As another example, in response to determining that the count of the lesion(s) in the second lesion detection result is greater than or equal to 1, the processing device 120 determines that the target object includes the lesion. As yet another example, in response to determining that the count of the lesion(s) in each of the first lesion detection result and the second lesion detection result is greater than or equal to 1, the processing device 120 determines that the target object includes the lesion. As a further example, in response to determining that both the first lesion information and the second lesion information indicate that the count of the lesion(s) is 0, the processing device 120 determines that the target object does not include the lesion.

According to some embodiments of the present disclosure, determining whether the target object includes the lesion based on both the first lesion information and the second lesion information effectively reduces the risk of missed and incorrect diagnoses caused by insufficient information from a single image.

In response to determining that the target object includes the lesion, the processing device 120 may perform operations 350 to 370. In response to determining that the target object does not include the lesion, the processing device 120 may directly generate a structured diagnostic report for the target object using a report generation model based on the first lesion information, the second lesion information, and the clinical information of the target object. The processing device 120 may generate the structured diagnostic report for the target object by performing an operation similar to operation 370. For example, the first lesion information, the second lesion information, and the clinical information of the target object may be input into the report generation model, and the report generation model may output the structured diagnostic report for the target object. More descriptions regarding generating the structured diagnostic report may be found in operation 370 and related descriptions thereof.

In 350, in response to determining that the target object includes the lesion, a target reconstructed image of the lesion may be generated using a simulation scanning model based on the raw scanning data and the reconstructed image. In some embodiments, operation 350 may be performed by the processing device 120 or the simulation scanning module 230.

The simulation scanning model is a trained machine learning model for simulating medical imaging. The simulation scanning model may simulate a plurality of types of medical imaging (e.g., high-resolution imaging, multi-phase scanning, and functional imaging). For example, the high-resolution imaging may include high-resolution computed tomography (HR-CT), high-resolution magnetic resonance imaging (HR-MRI), etc. The multi-phase scanning may include CT multi-phase scanning, MRI multi-phase dynamic contrast-enhanced scanning, or the like. The functional imaging may include diffusion-weighted imaging (DWI), perfusion-weighted imaging (PWI), PET scanning, or the like. In some embodiments, the processing device 120 may input the raw scanning data and the reconstructed image into the simulation scanning model, and the simulation scanning model may output the target reconstructed image of the lesion. In some embodiments, the input to the simulation scanning model further includes the first lesion information and the second lesion information.

In some embodiments, the simulation scanning model includes a plurality of models for simulating different medical imaging modalities. For example, the simulation scanning model may include a first simulation scanning model for simulating high-resolution imaging, a second simulation scanning model for simulating multi-phase scanning, and a third simulation scanning model for simulating functional imaging. The processing device 120 may select an appropriate simulation scanning model based on the first lesion information and the second lesion information. For example, in response to determining that the type of the lesion in the first lesion information or the second lesion information is a tumor, the processing device 120 may select the first simulation scanning model to obtain a high-resolution medical image of the lesion. As another example, in response to determining that the type of the lesion in the first lesion information or the second lesion information indicates that the lesion is a suspected vascular disease (e.g., coronary plaque), the processing device 120 may select the second simulation scanning model to obtain a multi-phase enhanced image of the lesion. As yet another example, in response to determining that the position of the lesion in the first lesion information or the second lesion information is located in the myocardium, the processing device 120 may select the third simulation scanning model to obtain an MRI myocardial perfusion image and determine quantitative perfusion parameters.

In some embodiments, the plurality of models for simulating different medical imaging modalities (e.g., the first simulation scanning model, the second simulation scanning model, and third simulation scanning model) may be integrated into a comprehensive simulation scanning model. The comprehensive simulation scanning model includes a model selector. The model selector is respectively connected to the plurality of models. The first lesion information, the second lesion information, the raw scanning data, and the reconstructed image may be input into the model selector. The model selector may select a model to be used from the plurality of models based on the first lesion information and the second lesion information. The model selector may further input the raw scanning data and the reconstructed image into the selected model to generate the target reconstructed image. For example, the model selector is connected to the first simulation scanning model, the second simulation scanning model, and the third simulation scanning model, respectively. The first lesion information, the second lesion information, the raw scanning data, and the reconstructed image are input into the model selector, and the model selector determines that the first simulation scanning model needs to be used based on the first lesion information and the second lesion information. The model selector then inputs the raw scanning data and the reconstructed image into the first simulation scanning model to generate a high-resolution medical image.

In some embodiments, the simulation scanning model may include various deep learning models. For example, the simulation scanning model may include a generative adversarial network (GAN), a diffusion model, a conditional variational autoencoder (CVAE), a nnUNet, a Mask R-CNN, a temporal analysis model (e.g., a 3DCNN model, a Long Short-Term Memory (LSTM) model), or the like.

In some embodiments, the simulation scanning model includes a simulation scanning module and an update module. The simulation scanning module is configured to generate an initial target reconstructed image based on the raw scanning data, the reconstructed image, the first lesion information, the second lesion information, and an initial scanning protocol parameter. The update module is configured to generate the target reconstructed image based on the initial target reconstructed image. In some embodiments, the raw scanning data, the reconstructed image, the first lesion information, the second lesion information, and the initial scanning protocol parameter may be input into the simulation scanning module, and the simulation scanning module outputs the initial target reconstructed image. Then, the initial target reconstructed image may be input into the update module, and the update module may output the target reconstructed image. In some embodiments, the initial target reconstructed image, the initial scanning protocol parameter, the first lesion information, and the second lesion information are collectively input into the update module, and the update module outputs the target reconstructed image.

The initial scanning protocol parameter refers to a scanning protocol parameter used to perform a scan on the target object to obtain the raw scanning data. For CT scanning, the scanning protocol parameter may include a tube voltage (kV), a tube current (mAs), a slice thickness, a reconstruction kernel, or the like. For MRI scanning, the scanning protocol parameter may include a sequence type, an echo time (TE), a repetition time (TR), a flip angle, or the like. In some embodiments, the initial scanning protocol parameter may be manually determined by the user (e.g., an imaging physician) based on the first lesion information and the second lesion information. In some embodiments, the processing device 120 may automatically match or generate the initial scanning protocol parameter based on the first lesion information and/or the second lesion information via a built-in protocol knowledge base or a protocol recommendation model.

In some embodiments, the simulation scanning module may include a simulation scanning unit and an enhancement unit connected in sequence. The simulation scanning unit is configured to simulate the scanning process of the target object. The raw scanning data, the reconstructed image, the first lesion information, the second lesion information, and the initial scanning protocol parameter may be input into the simulation scanning unit. The simulation scanning unit may perform a simulation scanning process to output an initial simulated image. In some embodiments, the simulation scanning unit may be a hard-coded unit based on explicit physical formulas. For example, for CT scanning, the simulation scanning unit is a differentiable computed filtered back-projection unit. For MRI scanning, the simulation scanning unit is a differentiable magnetic resonance forward unit, which includes a differentiable Bloch equation solver and differentiable k-space sampling and Fourier transform layers. The first lesion information, the second lesion information, and the initial simulated image are input into the enhancement unit. The enhancement unit may enhance the initial simulated image to generate the initial target reconstructed image. The enhancement unit may learn complex texture details, realistic noise distribution patterns, and subtle contrast variations between tissues that are not captured by the simulation scanning unit, thereby generating an enhanced image that is visually highly realistic and rich in detail, i.e., the initial target reconstructed image. In some embodiments, the enhancement unit employs a neural network with an encoder-decoder structure. The enhancement unit may adopt a conditional generative model, such as a conditional diffusion model network, a conditional generative adversarial network, or the like.

Figure 8:
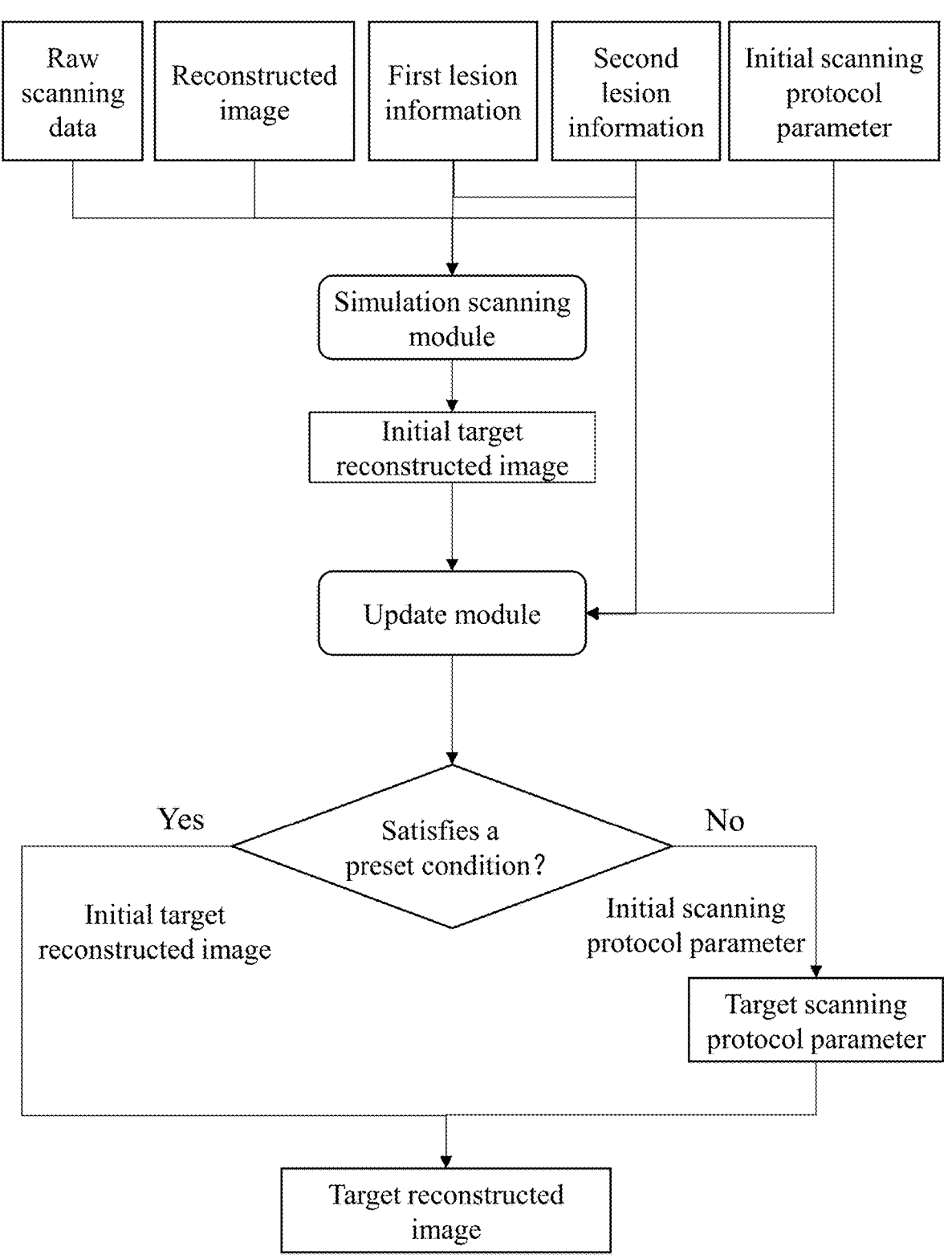
FIG. 8 is a schematic diagram illustrating an exemplary process for generating a target reconstructed image using a simulation scanning model according to some embodiments of the present disclosure.

In some embodiments, the update module may determine whether the initial target reconstructed image satisfies a preset condition. In response to determining that the initial target reconstructed image does not satisfy the preset condition, the update module may update the initial target reconstructed image to generate the target reconstructed image. In response to determining that the initial target reconstructed image satisfies the preset condition, the update module may directly output the initial target reconstructed image as the target reconstructed image. For example, FIG. 8 is a schematic diagram illustrating an exemplary process for generating a target reconstructed image using a simulation scanning model according to some embodiments of the present disclosure. As shown in FIG. 8, the raw scanning data, the reconstructed image, the first lesion information, the second lesion information, and the initial scanning protocol parameter are input into the simulation scanning module, and the simulation scanning module outputs the initial target reconstructed image. Subsequently, the initial target reconstructed image, the initial scanning protocol parameter, the first lesion information, and the second lesion information are input into the update module. The update module may determine whether the initial target reconstructed image satisfies the preset condition. In some embodiments, the update module may analyze whether one or more parameters of the initial target reconstructed image satisfy the preset condition. Exemplary parameters of the initial target reconstructed image include noise, contrast, resolution, etc. For example, the update module may determine whether the noise is less than a noise threshold, whether the resolution is greater than a resolution threshold, and whether the contrast is within a preset contrast range. In response to determining that the noise is less than the noise threshold, the noise satisfies the preset condition. In response to determining that the noise is not less than the noise threshold, the noise does not satisfy the preset condition. In response to determining that the resolution is greater than the resolution threshold, the resolution satisfies the preset condition. In response to determining that the resolution is not greater than the resolution threshold, the resolution does not satisfy the preset condition. In response to determining that the contrast is within the preset contrast range, the contrast satisfies the preset condition. In response to determining that the contrast is not within the preset contrast range, the contrast does not satisfy the preset condition. In response to determining that all parameters satisfy the preset condition, the update module may determine that the initial target reconstructed image satisfies the preset condition and directly output the initial target reconstructed image as the target reconstructed image. In response to determining that at least one parameter does not satisfy the preset condition, the update module may determine that the initial target reconstructed image does not satisfy the preset condition and update the initial target reconstructed image. For example, the update module may perform operations (e.g., denoising, sharpening, and contrast stretching) on the initial target reconstructed image.

The value of the initial scanning protocol parameter may affect the quality of the initial target reconstructed image. For example, the radiation dose parameter (mAs) in the initial scanning protocol parameter is too low, resulting in high noise. As another example, the slice thickness is too large, causing blurring of lesion edges. To address these issues, in some embodiments, as shown in FIG. 8, in response to determining that the initial target reconstructed image does not satisfy the preset condition, the update module may adjust the initial scanning protocol parameter to generate a target scanning protocol parameter. Furthermore, the update module may generate the target reconstructed image based on the target scanning protocol parameter. For example, the raw scanning data, the reconstructed image, the first lesion information, the second lesion information, and the target scanning protocol parameter may be input into the simulation scanning module to generate an updated target reconstructed image. Then, the updated target reconstructed image is input into the update module, and the update module determines whether the updated target reconstructed image satisfies the preset condition. The above operations are repeated until the obtained updated target reconstructed image satisfies the preset condition, and the update module may output the updated target reconstructed image that satisfies the preset condition as the target reconstructed image. As another example, the update module may directly generate an updated target reconstructed image based on the initial target reconstructed image and the target scanning protocol parameter, and determine whether the updated target reconstructed image satisfies the preset condition. The above operations are repeated until the updated target reconstructed image satisfies the preset condition. The update module may then output the updated target reconstructed image that satisfies the preset condition as the target reconstructed image.

In some embodiments, the processing device 120 obtains the simulation scanning model by a process similar to obtaining the raw data analysis model. Merely by way of example, the processing device 120 may obtain a plurality of third training samples. Each of the plurality of third training samples may include sample raw data of a sample object, a sample reconstructed image, and a reference reconstructed image. The reference reconstructed image serves as a label or gold standard for model training. In some embodiments, each of the plurality of third training samples further includes sample first lesion information, sample second lesion information, and a sample scanning protocol parameter. The sample raw data refers to original data (e.g., projection data for CT or k-space data for MRI) obtained by scanning the sample object using the medical imaging device 110. The sample reconstructed image is generated based on the sample raw data. The sample first lesion information is generated based on the sample raw data. The sample second lesion information may be generated based on the sample reconstructed image. In some embodiments, the sample first lesion information and the sample second lesion information may be determined by performing operations similar to operations 320 and 330. The sample scanning protocol parameter refers to a scanning protocol parameter used to scan the sample object to obtain the sample raw data. The reference reconstructed image may be generated by performing medical imaging on the sample object using the medical imaging device 110. For example, for the first simulation scanning model, the reference reconstructed image may be generated by performing high-resolution imaging on the sample object using the medical imaging device 110 and performing image reconstruction based on the obtained raw scanning data. As another example, for the second simulation scanning model, the reference reconstructed image may be generated by performing multi-phase scanning on the sample object using the medical imaging device 110 and performing image reconstruction based on the obtained raw scanning data. As yet another example, for the third simulation scanning model, the reference reconstructed image may be generated by performing functional imaging on the sample object using the medical imaging device 110 and performing image reconstruction based on the obtained raw scanning data. Furthermore, the processing device 120 may generate the simulation scanning model by training a third preliminary model using the plurality of third training samples. The third preliminary model refers to an untrained machine learning model. The obtaining process and the structure of the third preliminary model are similar to those of the simulation scanning model and will not be elaborated here. During training, the sample reconstructed image and the sample raw data (or the sample reconstructed image, the sample raw data, the sample first lesion information, the sample second lesion information, and the sample scanning protocol parameter) in the plurality of third training samples may serve as model input of the third preliminary model, the reference reconstructed image corresponding to each of the plurality of third training samples may serve as a training label, and parameters of the third preliminary model may be iteratively updated until a termination condition is satisfied. Any suitable loss function (e.g., MSE) and any suitable optimizer (e.g., Adam optimizer) may be used to train the third preliminary model to obtain the simulation scanning model.

In some embodiments, the simulation scanning model may be generated by training the third preliminary model using the plurality of third training samples based on a first loss function and a second loss function. During training, for each of the plurality of third training samples, a value of the first loss function (also referred to as a first loss value) is determined based on the reference reconstructed image and a predicted target reconstructed image generated by the third preliminary model. For example, a difference between the predicted target reconstructed image and the reference reconstructed image may serve as the value of the first loss function. A value of the second loss function (also referred to as a second loss value) is determined based on predicted raw scanning data and the sample raw data. For example, a difference between the predicted raw scanning data and the sample raw data may serve as the value of the second loss function. The predicted raw scanning data is determined based on the predicted target reconstructed image. For example, the predicted target reconstructed image may be converted into a digital model representing a virtual anatomical structure of the sample object. Furthermore, a differentiable forward imaging computational model is constructed based on the sample scanning protocol parameter, and virtual imaging computation is performed on the digital model via the differentiable forward imaging computational model to obtain the predicted raw scanning data. Furthermore, a total loss value is determined based on the first loss value and the second loss value. For example, an average of the first loss value and the second loss value may be determined as the total loss value. As another example, a weighted sum of the first loss value and the second loss value may be calculated to determine the total loss value. Then, parameters of the third preliminary model are updated based on the total loss value until a preset termination condition is satisfied.

In some embodiments, the training process of the third preliminary model may include a first training phase and a second training phase performed sequentially. In some embodiments, in the first training phase, only the first loss function is used to train the third preliminary model. In the second training phase, part of model parameters obtained in the first training phase are fixed, while the first loss function and the second loss function are used jointly for training to adjust the remaining model parameters. In some embodiments, in the first training phase, emphasis may be placed on image quality reconstruction, and a weight corresponding to the first loss value is greater than a weight corresponding to the second loss value. In the second training phase, the weight corresponding to the second loss is greater than the weight corresponding to the first loss to enhance the self-consistency constraint.

In conventional procedures, after obtaining the reconstructed image, sequential assessments by a radiologist and a clinical physician are required to determine whether an additional scan targeting the lesion (e.g., a high-resolution scan or a contrast-enhanced scan) is necessary. If the additional scan is deemed necessary, the clinical physician issues another examination order, followed by the additional scan. This constitutes a sequential, labor-intensive process that leads to prolonged diagnostic and treatment cycle and low efficiency. In the present disclosure, after determining that the target object includes a lesion, a simulated scan is directly performed via the simulation scanning model without requiring actual scanning, thereby greatly improving diagnostic efficiency. By replacing an additional physical scan with a simulated scan, the target object is spared unnecessary radiation exposure, contrast agent injection risks, and additional economic burdens.

In 360, third lesion information may be obtained by performing feature extraction on the target reconstructed image. In some embodiments, operation 360 may be performed by the processing device 120 or the determination module 220.

The third lesion information refers to information related to the lesion of the target object. The third lesion information includes a third lesion detection result. The third lesion detection result includes the size of the lesion, the severity of the lesion, the type of the lesion (e.g., solid tumor, cyst, and hemorrhage), the position of the lesion, the density of the lesion, or the like.

In some embodiments, the third lesion information further includes a third confidence map. The third confidence map includes a confidence of each pixel in the target reconstructed image. The confidence of the pixel may be in a range of 0 to 1. A higher score of the confidence for the pixel indicates a higher confidence for the pixel, that is, the signal from the pixel is more likely to originate from the anatomical structure of the target object and less likely to originate from noise or artifacts.

In some embodiments, the third lesion information is determined by processing the target reconstructed image using a lesion analysis model. The lesion analysis model is a trained machine learning model. The lesion analysis model refers to a model that determines lesion information based on the target reconstructed image. In some embodiments, the processing device 120 may input the target reconstructed image into the lesion analysis model, and the lesion analysis model may output the third lesion information. In some embodiments, other manners may be used to obtain the third lesion information. For example, the target reconstructed image may be segmented using an image segmentation algorithm to obtain information (e.g., the position of the lesion, the type of the lesion, and the size of the lesion). The type of the lesion, the probability that the lesion is malignancy, etc., may be determined manually.

In some embodiments, the lesion analysis model may be similar to the image analysis model. The lesion analysis model may adopt a structure similar to the image analysis model. For example, the lesion analysis model includes the vision-language large model.

In some embodiments, the processing device 120 obtains the lesion analysis model in a process similar to obtaining the raw data analysis model. Merely by way of example, the processing device 120 may obtain a plurality of fourth training samples. Each of the plurality of fourth training samples may include a second sample reconstructed image of a sample object and third label lesion information. The third label lesion information serves as a label or gold standard for model training. In some embodiments, the process for generating the reference reconstructed image in operation 350 may be used to generate the second sample reconstructed image. The third label lesion information may be confirmed manually by the user. Furthermore, the processing device 120 may generate the lesion analysis model by training a fourth preliminary model based on the plurality of fourth training samples. The fourth preliminary model refers to an untrained machine learning model. The obtaining process and the structure of the fourth preliminary model are similar to those of the lesion analysis model and will not be elaborated here. During training, the second sample reconstructed image in the training samples may serve as model input of the fourth preliminary model, the third label lesion information corresponding to each of the plurality of fourth training samples may serve as a training label, and parameters of the fourth preliminary model may be iteratively updated until a termination condition is satisfied. Any suitable loss function (e.g., MSE) and any suitable optimizer (e.g., Adam optimizer) may be used to train the fourth preliminary model to obtain the lesion analysis model.

In 370, a structured diagnostic report for the target object may be generated using a report generation model based on the first lesion information, the second lesion information, the third lesion information, and the clinical information. In some embodiments, operation 370 may be performed by the processing device 120 or the report generation module 240.

The structured diagnostic report for the target object includes a diagnostic result. The diagnostic result at least includes a lesion assessment result. The lesion assessment result refers to a final judgment on a nature of the lesion. For example, the lesion assessment result may indicate that the target object has primary lung adenocarcinoma, a hepatic cyst, a benign nodule, or the like. In some embodiments, the diagnostic result further includes one or more of a diagnostic confidence index, a clinical action suggestion, etc. The diagnostic confidence index refers to a quantified confidence score (e.g., 95%), indicating a degree of certainty the report generation model has regarding the diagnostic result. The clinical action suggestion refers to a proposed subsequent treatment suggestion for the lesion. For example, the clinical action suggestion may be surgical resection, regular follow-up, further PET-CT examination, or the like.

In some embodiments, the structured diagnostic report further includes a traceability basis. The traceability basis indicates information on which the diagnostic result is based. For example, the traceability basis for the size of the lesion may be an average value of the sizes of the lesions in the first lesion information, the second lesion information, and the third lesion information. As another example, the type of the lesion may be the type of the lesion in the third lesion information. As yet another example, the traceability basis for the size of the lesion may be a weighted average value of severity levels of the lesions in the first lesion information, the second lesion information, and the third lesion information. In some embodiments, the structured diagnostic report further includes a consistency detection result. The consistency detection result may indicate whether there is a conflict among the first lesion detection result, the second lesion detection result, and the third lesion detection result, that is, whether the first, second, and third lesion detection results are consistent.

Currently, physicians select treatment plans (e.g., chemotherapy regimens or targeted therapy regimens) mainly based on population data from clinical trials and clinical experience, lacking prediction of the specific efficacy for the individual patient. The treatment effect can only be assessed weeks or months after treatment through re-examination. If the treatment effect is poor, the patient has already suffered unnecessary toxic side effects and delayed treatment timing. Furthermore, it is difficult for physicians to intuitively demonstrate to patients and their families the potential different outcomes of different treatment plans, affecting shared decision-making.

In some embodiments, the structured diagnostic report for the target object further includes a treatment evaluation result. The treatment evaluation result may include treatment evaluation results for one or more reference treatment plans. In some embodiments, the treatment evaluation result includes, for each reference treatment plan of the one or more reference treatment plans, at least one of an efficacy prediction indicator, a predicted medical image of the lesion, a side effect assessment, and a recommendation index. In some embodiments, the treatment evaluation result corresponding to each reference treatment plan may include efficacy prediction indicators, predicted medical images of the lesion, side effect assessments, etc., corresponding to one or more post-treatment evaluation time points. The efficacy prediction indicator includes at least one quantitative parameter characterizing an expected degree of response of the lesion to a treatment plan. The efficacy prediction indicator may include a predicted tumor volume change rate, a predicted percentage reduction in the maximum diameter of the tumor, a predicted efficacy classification according to the Response Evaluation Criteria in Solid Tumors (RECIST) or similar standards (e.g., complete response, partial response, stable disease, and progressive disease), predicted survival indicators (e.g., progression-free survival or disease-free survival), or the like. In some embodiments, the efficacy prediction indicator may include a tumor volume change curve, a key biomarker change chart, or the like. The tumor volume change curve refers to a response curve of a tumor over time. The key biomarker change chart may include predicted trend changes in indicators such as CEA, CA199, etc. The predicted medical image of the lesion refers to a medical image, simulated based on the reference treatment plan, that represents the lesion at a specific time point after treatment (e.g., a CT image or MRI image after 4 weeks of treatment). The side effect assessment may include a probability of occurrence of a specific side effect, a severity grade, or the like. In some embodiments, the recommendation index for each reference treatment plan may be determined by synthesizing evaluation results from a plurality of evaluation time points. In some embodiments, for each evaluation time point, an initial recommendation index corresponding to that evaluation time point may be determined based on the efficacy prediction indicator, the predicted medical image of the lesion, the side effect assessment at the evaluation time point. Then, the recommendation index for each reference plan is determined based on the initial recommendation index corresponding to each evaluation time point. For example, an average value of a plurality of initial recommendation indices may be determined as the recommendation index.

The report generation model is a trained machine learning model. The report generation model refers to a model for generating the structured diagnostic report. In some embodiments, the processing device 120 may input the first lesion detection result, the second lesion detection result, the third lesion detection result, and the clinical data into the report generation model, and the report generation model may output the structured diagnostic report.

In some embodiments, the processing device 120 may determine a first weight corresponding to the first lesion detection result, a second weight corresponding to the second lesion detection result, and a third weight corresponding to the third lesion detection result based on the clinical information, the first confidence map, the second confidence map, and the third confidence map. In some embodiments, for each weight of the first weight, the second weight, and the third weight, a value of the weight is in a range of 0 to 1. The sum of the values of the first weight, the second weight, and the third weight may not equal 1.

Figure 5:
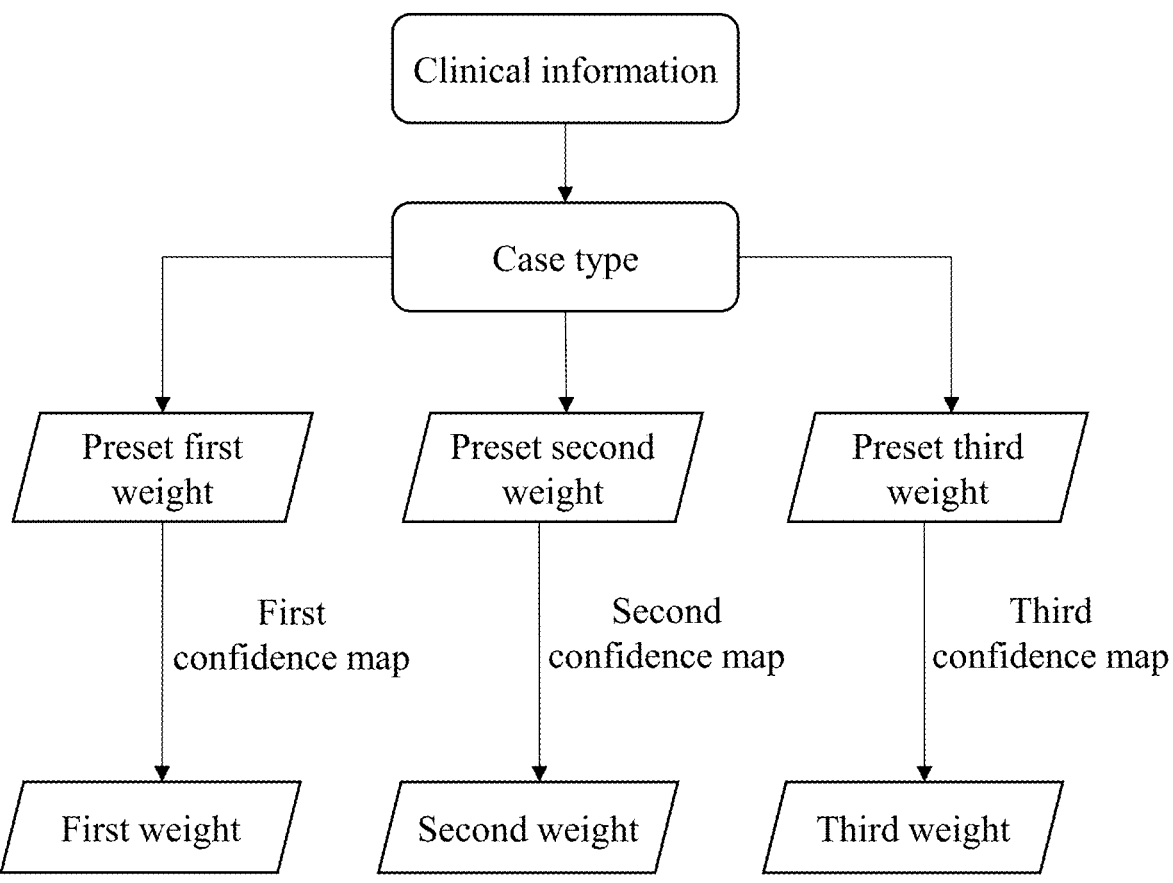
FIG. 5 is a schematic diagram illustrating an exemplary process for determining a first weight, a second weight, and a third weight according to some embodiments of the present disclosure.

FIG. 5 is a schematic diagram illustrating an exemplary process for determining a first weight, a second weight, and a third weight according to some embodiments of the present disclosure. As shown in FIG. 5, the processing device 120 may determine a case type of the target object based on the clinical information. The case type may be classified in different ways. For example, according to the type and the position of the lesion, the case type may include lung cancer, liver cancer, vascular disease (e.g., embolism, stenosis), trauma, hemorrhage, or the like. As another example, according to disease progression, the case type may include early-stage lesions, intermediate-stage lesions, and late-stage lesions. For example, if a preliminary diagnosis by a physician in the clinical information includes information such as "suspected lung cancer," the processing device 120 may determine that the case type of the target object is lung cancer. As another example, if current symptom information in the clinical information includes information such as "sudden chest pain, elevated D-dimer", the processing device 120 may determine that the case type of the target object is pulmonary embolism. As yet another example, if the current symptom information and medical history in the clinical information include information such as "history of hepatitis B, elevated AFP", the processing device 120 may determine that the case type of the target object is liver cancer. As a further example, according to prevalence, the case type may include common diseases, rare diseases, or the like.

Furthermore, the processing device 120 may determine a preset first weight corresponding to the first lesion detection result, a preset second weight corresponding to the second lesion detection result, and a preset third weight corresponding to the third lesion detection result based on the case type. For example, if the case type of the target object is lung cancer, since morphological analysis of the reconstructed image by the image analysis model is relatively accurate for diagnosing lung cancer, the preset second weight may be assigned a higher value, such as 1. As another example, if the case type of the target object is liver cancer, since perfusion information or enhancement dynamics provided by functional imaging or contrast-enhanced scanning are relatively accurate for diagnosing liver cancer, the preset third weight may be assigned a higher value, such as 1. As yet another example, if the case type of the target object is an early-stage lesion, the early signal detection capability provided by the raw data analysis model may be relatively accurate for its diagnosis, so the preset first weight may be assigned a higher value, such as 1. In some embodiments, a mapping relationship between different disease types and weight assignment schemes (i.e., the preset weights corresponding to the first, second, and third lesion detection results, respectively) may be preset. The processing device may determine the preset first weight, the preset second weight, and the preset third weight based on the mapping relationship.

Then, the processing device 120 may determine the first weight, the second weight, and the third weight by adjusting the preset first weight, the preset second weight, and the preset third weight based on the first confidence map, the second confidence map, and the third confidence map. In some embodiments, the processing device 120 may determine a first average confidence based on the first confidence map. The first average confidence may be an average value of confidences of all raw data points. In response to determining that the first average confidence is below a first confidence threshold, the processing device 120 lowers the preset first weight. In response to determining that the first average confidence is above a second confidence threshold, the processing device 120 raises the preset first weight. In response to determining that the first average confidence is between the first confidence threshold and the second confidence threshold, the processing device 120 designates the preset first weight as the first weight. The processing device 120 may determine a second average confidence based on the second confidence map. The second average confidence may be an average value of confidences of all pixels in the reconstructed image. In some embodiments, the second average confidence may be the average of the confidences of pixels in the reconstructed image corresponding to the lesion. In response to determining that the second average confidence is below a third confidence threshold, the processing device 120 lowers the preset second weight. In response to determining that the second average confidence is above a fourth confidence threshold, the processing device 120 raises the preset second weight. In response to determining that the second average confidence is between the third confidence threshold and the fourth confidence threshold, the processing device 120 designates the preset second weight as the second weight. The processing device 120 may determine a third average confidence based on the third confidence map. The third average confidence may be an average value of confidences of pixels in the target reconstructed image corresponding to the lesion. In response to determining that the third average confidence is below a fifth confidence threshold, the processing device 120 lowers the preset third weight. In response to determining that the third average confidence is above a sixth confidence threshold, the processing device 120 raises the preset third weight. In response to determining that the third average confidence is between the fifth confidence threshold and the sixth confidence threshold, the processing device 120 designates the preset third weight as the third weight. In some embodiments, the processing device 120 may obtain a fourth weight corresponding to the clinical information. The fourth weight may be set as needed. In some embodiments, since the clinical information is confirmed, the fourth weight may be 1.

Furthermore, the processing device 120 may generate the structured diagnostic report for the target object by processing the first lesion detection result, the second lesion detection result, the third lesion detection result, the first weight, the second weight, the third weight, the fourth weight, and the clinical information using the report generation model. In some embodiments, the processing device 120 may input the first lesion detection result, the second lesion detection result, the third lesion detection result, the first weight, the second weight, the third weight, the fourth weight, and the clinical information into the report generation model, and the report generation model may output the structured diagnostic report.

In some embodiments, in response to determining that historical diagnostic data relating to the lesion exists, the processing device 120 may determine lesion change information based on the historical diagnostic data, the first lesion information, the second lesion information, and the third lesion information. The lesion change information may include changes in the size of the lesion, changes in the count of the lesion(s), changes in the type of the lesion, changes in the position of the lesion, changes in the severity of the lesion, or the like. Further, the processing device 120 generates the structured diagnostic report for the target object by processing the first lesion information, the second lesion information, the third lesion information, the clinical information, and the lesion change information using the report generation model. For example, the processing device 120 may input the first lesion detection result, the second lesion detection result, the third lesion detection result, the first weight, the second weight, the third weight, the fourth weight, the clinical information, and the lesion change information into the report generation model, and the report generation model may output the structured diagnostic report. By incorporating historical diagnostic data of the lesion and adding lesion change information as input to the report generation model, a more accurate diagnostic report can be obtained.

In some embodiments, the report generation model includes a feature fusion module and a structured report generation module. The feature fusion module is configured to determine a consistency detection result, fused feature information, and an initial traceability basis corresponding to the fused feature information by performing consistency detection and feature fusion based on the first lesion detection result, the second lesion detection result, the third lesion detection result, the first weight, the second weight, the third weight, and the clinical information. The structured report generation module is configured to determine the diagnostic result based on the fused feature information, and determine the traceability basis based on the initial traceability basis. The structured report generation module is also configured to generate the structured diagnostic report based on the consistency detection result, the diagnostic result, and the traceability basis.

Figure 6:
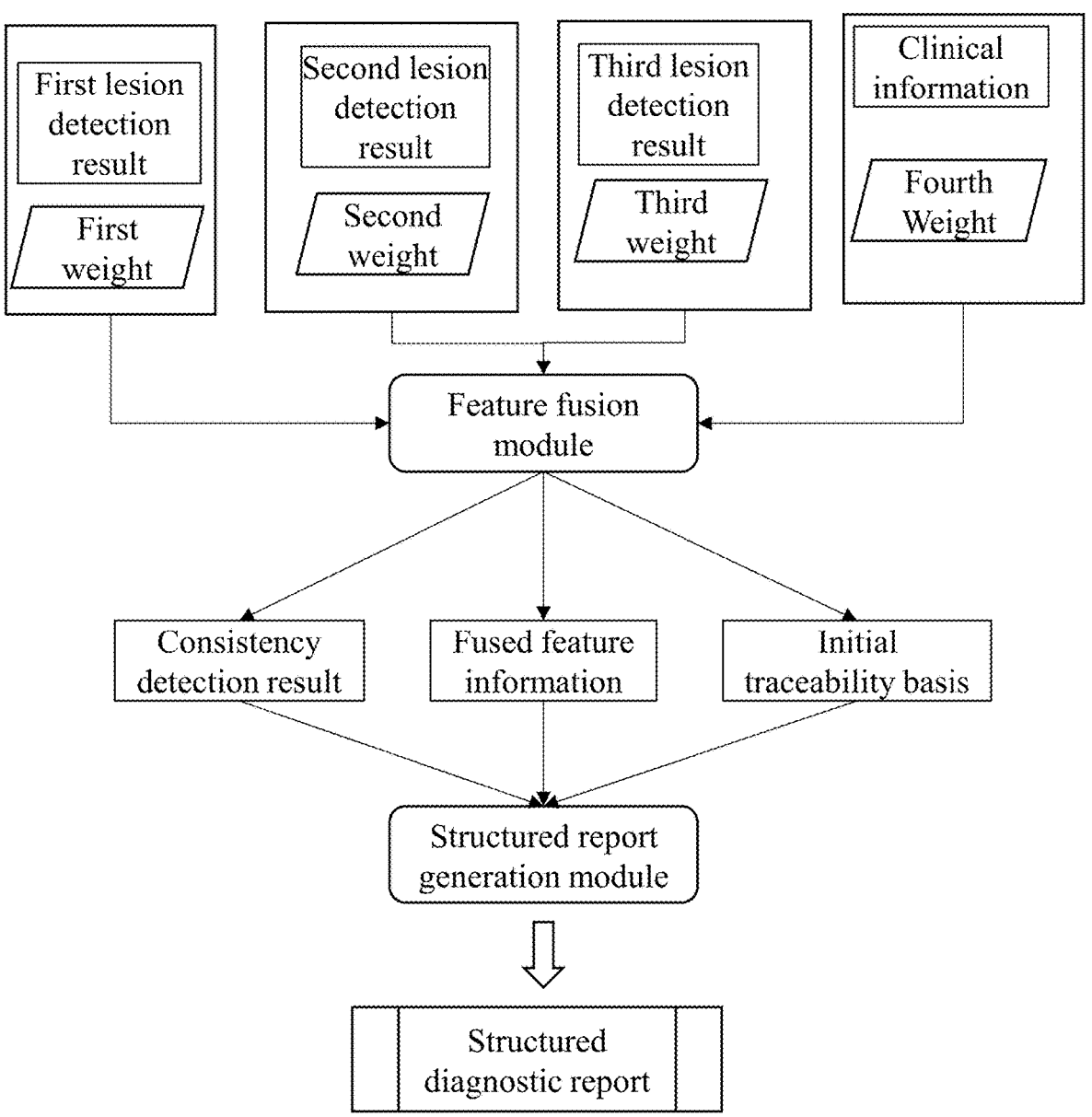
FIG. 6 is a schematic diagram illustrating an exemplary process for determining a structured diagnostic report using a report generation model according to some embodiments of the present disclosure.

FIG. 6 is a schematic diagram illustrating an exemplary process for determining a structured diagnostic report using a report generation model according to some embodiments of the present disclosure. As shown in FIG. 6, the processing device 120 may input the first lesion detection result, the second lesion detection result, the third lesion detection result, the clinical information, the first weight, the second weight, the third weight, and the fourth weight into the feature fusion module. The feature fusion module may perform consistency detection on each feature item in the first lesion detection result, the second lesion detection result, and the third lesion detection result to generate the consistency detection result. The feature item may include the count of the lesion(s), the size of the lesion, the severity of the lesion, the type of the lesion, the position of the lesion, or the like. The consistency detection result may indicate whether results of corresponding identical feature items in the first lesion detection result, the second lesion detection result, and the third lesion detection result are consistent (or conflict). For example, in response to determining that the sizes of the lesion and the positions of the lesion among the second lesion detection result and the third lesion detection result are not the same, the consistency detection result includes inconsistency (i.e., conflict) in lesion size and lesion position. As another example, for the same lesion, in response to determining that the types of the lesion among the first lesion detection result, the second lesion detection result, and the third lesion detection result are the same, the consistency detection result includes consistency (i.e., no conflict) in lesion type. As yet another example, for the same lesion, in response to determining that a difference in severities of the lesion among the first lesion detection result, the second lesion detection result, and the third lesion detection result is less than a threshold, the consistency detection result includes consistency (i.e., no conflict) in lesion severity. In some embodiments, the feature fusion module may align the corresponding feature items in the first lesion detection result, the second lesion detection result, and the third lesion detection result. Furthermore, for each feature item, the feature fusion module may perform weighted fusion based on values of the feature item in the first lesion detection result, the second lesion detection result, the third lesion detection result, and the clinical information and the corresponding first, second, third, and fourth weights to obtain fused information for the feature item. Then, the feature fusion module concatenates the fused information of each feature item to generate fused feature information. The initial traceability basis includes a source of the fused information for each feature item and the weights used during the fusion.

Then, the consistency detection result, the fused feature information, and the initial traceability basis may be input into the structured report generation module, which may output the structured diagnostic report. In some embodiments, the structured report generation module may determine the diagnostic result based on the fused feature information. For example, the structured report generation module may designate the lesion size, the lesion position, and the lesion type in the fused feature information as the lesion size, the lesion position, and the lesion type in the diagnostic result. As another example, the structured report generation module may determine whether the lesion is benign or malignant based on the severity of the lesion. As yet another example, the structured report generation module may determine whether the lesion is benign or malignant based on one or more of the lesion size, the lesion severity, the lesion type, or the like. For example, a greater lesion severity and a larger size may indicate a malignant lesion. As another example, if the type of the lesion is a cyst, the lesion may be determined as benign. In some embodiments, the structured report generation module may determine the diagnostic result by referring to domain knowledge bases, medical guidelines, medical standards, or the like.

The structured report generation module may determine the traceability basis based on the initial traceability basis. In some embodiments, the traceability basis includes sources of fused information in the initial traceability basis whose weights exceed a specific threshold. For example, if the initial traceability basis indicates that the lesion type is derived from the first, second, and third lesion detection results, all with weights of 1, then the traceability basis indicates that the lesion type originates from the first, second, and third lesion detection results. As another example, if the initial traceability basis indicates that the lesion position is derived from the second and third lesion detection results, both with weights of 1, then the traceability basis indicates that the lesion position originates from the second and third lesion detection results. As yet another example, if the initial traceability basis indicates that the lesion size is derived from the second and third lesion detection results with weights of 0.4 and 0.8, respectively, the traceability basis indicates that the lesion size originates from the third lesion detection result. For example, if the initial traceability basis indicates that lesion severity is derived from the first, second, and third lesion detection results with weights of 0.2, 0.4, and 0.9, respectively, the traceability basis indicates that lesion severity originates from the third lesion detection result.

Finally, the structured report generation module arranges the consistency detection result, the diagnostic result, and the traceability basis in a predefined format to generate the structured diagnostic report.

In some embodiments, the feature fusion module may include a multilayer perceptron, a deep neural network, a gradient boosting decision tree model, a Bayesian network, or the like. The structured report generation module may include a Transformer-based autoregressive language model, a retrieval-augmented generation model, a large language model, or the like.

According to some embodiments of the present disclosure, integrating the consistency detection result, the diagnostic result, and the traceability basis into the structured diagnostic report significantly enhances the credibility, traceability, and practicality of the structured diagnostic report. The traceability basis makes the model's decision-making process transparent, eliminating "black box" concerns. Consistency detection proactively reveals uncertainties, warns of risks, and stimulates human-machine collaborative review. Ultimately, the clear output of diagnostic results empowers physicians to quickly focus on key information, greatly improving the reliability of diagnostic efficiency, while providing a complete audit trail for model compliance monitoring and continuous optimization.

As mentioned above, the structured diagnostic report for the target object further includes a treatment evaluation result. In some embodiments, the report generation model further includes a treatment prediction module. The treatment prediction module is configured to generate the treatment evaluation result. In some embodiments, the first lesion detection result, the second lesion detection result, the third lesion detection result, the clinical information, and the diagnostic result may be input into the treatment prediction module, and the treatment prediction module may output the treatment evaluation result. More descriptions regarding the treatment prediction module generating the treatment evaluation result may be found in FIG. 9 and related descriptions thereof. The structured report generation module is further configured to generate the structured diagnostic report based on the treatment evaluation result, the consistency detection result, the diagnostic result, and the traceability basis. For example, the structured report generation module arranges the treatment evaluation result, the consistency detection result, the diagnostic result, and the traceability basis in a predefined format to generate the structured diagnostic report.

In some embodiments, the processing device 120 obtains the report generation model by performing a process similar to obtaining the raw data analysis model. Merely by way of example, the processing device 120 may obtain a plurality of fifth training samples. Each of the plurality of fifth training samples may include a sample first lesion detection result of a sample object and a sample first weight corresponding to the sample first lesion detection result, a sample second lesion detection result and a sample second weight corresponding to the sample second lesion detection result, a sample third lesion detection result and a sample third weight corresponding to the sample third lesion detection result, sample clinical information of the sample object and a sample fourth weight corresponding to the sample clinical information, and a reference structured diagnostic report. The reference structured diagnostic report may serve as a label or gold standard for model training. In some embodiments, the sample first lesion detection result may be generated using a process for generating the first lesion information in operation 320. In some embodiments, the sample second lesion detection result may be generated using a process for generating the second lesion information in operation 330. In some embodiments, the sample third lesion detection result may be generated using a process for generating the third lesion information in operation 360. In some embodiments, the processes for generating the first weight, the second weight, the third weight, and the fourth weight described above may be used to determine the sample first weight, the sample second weight, the sample third weight, and the sample fourth weight. In some embodiments, each of the plurality of fifth training samples may further include sample raw data of the sample object, a sample reconstructed image, and a sample treatment plan. The sample raw data refers to original data (e.g., projection data for CT, and k-space data for MRI) obtained by scanning the sample object using the medical imaging device 110. The sample reconstructed image is generated based on the sample raw data. The sample treatment plan refers to a treatment plan used to treat the sample object. The reference structured diagnostic report may be confirmed manually by the user.

Furthermore, the processing device 120 may generate the report generation model by training an initial fifth preliminary model based on the plurality of fifth training samples. The fifth preliminary model refers to an untrained machine learning model. The obtaining process and the structure of the fifth preliminary model are similar to those of the report generation model and will not be elaborated here. During training, the sample first lesion detection result, the sample first weight, the sample second lesion detection result, the sample second weight, the sample third lesion detection result, the sample third weight, the sample clinical information, and the sample fourth weight in the plurality of fifth training samples may serve as model input of the fifth preliminary model, the reference structured diagnostic report corresponding to each of the plurality of fifth training sample may serve as a training label, and parameters of the fifth preliminary model may be iteratively updated until a termination condition is satisfied. Any suitable loss function (e.g., MSE) and any suitable optimizer (e.g., Adam optimizer) may be used to train the fifth preliminary model to obtain the report generation model.

It should be noted that the above description regarding process 300 is provided merely as example and illustration and does not limit the applicable scope of the present disclosure. For those skilled in the art, various modifications and changes may be made to process 300 under the guidance of the present disclosure. However, such modifications and changes remain within the scope of the present disclosure.

Figure 4:
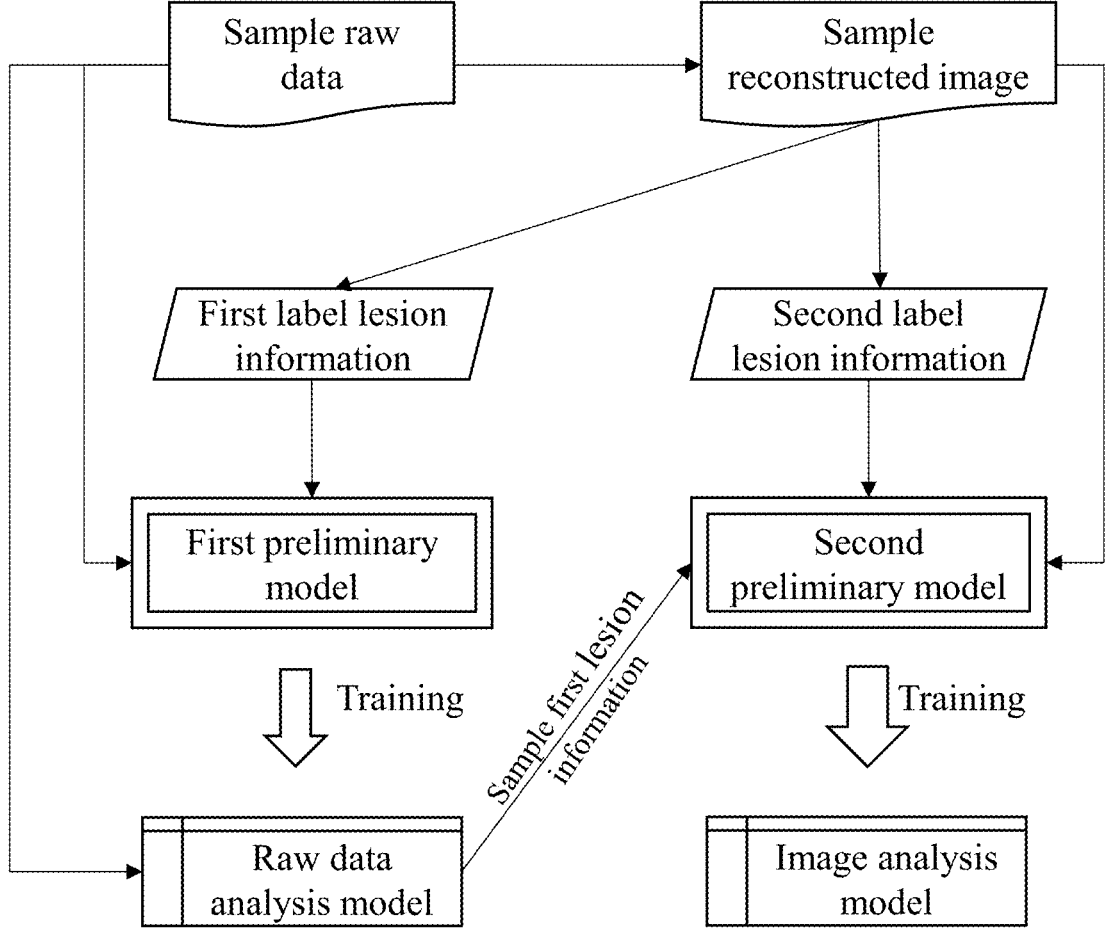
FIG. 4 is a schematic diagram illustrating an exemplary process for training a raw data analysis model and an image analysis model according to some embodiments of the present disclosure.

FIG. 4 is a schematic diagram illustrating an exemplary process for training a raw data analysis model and an image analysis model according to some embodiments of the present disclosure. The training process of FIG. 4 may be performed by the processing device 120 or the model training module 250.

The raw data analysis model and the image analysis model may be obtained by sequentially training the first preliminary model and the second preliminary model. As shown in FIG. 4, the processing device 120 may obtain sample raw data of a sample object, a sample reconstructed image corresponding to the sample raw data, first label lesion information corresponding to the sample reconstructed image, and second label lesion information corresponding to the sample reconstructed image. Further, the processing device 120 may obtain the raw data analysis model by training the first preliminary model using the sample raw data and the first label lesion information. Then, the processing device 120 may determine sample first lesion information corresponding to the sample raw data based on the sample raw data and the raw data analysis model. In some embodiments, the sample raw data may be input into a trained raw data analysis model to obtain the sample first lesion information. Finally, the processing device 120 may obtain the image analysis model by training the second preliminary model using the sample reconstructed image, the sample first lesion information, and the second label lesion information. More descriptions regarding training the first preliminary model to generate the raw data analysis model may be found in operation 320 and related descriptions thereof. More descriptions regarding training the second preliminary model to generate the image analysis model may be found in operation 330 and related descriptions thereof. In some embodiments, the processing device 120 may obtain the sample raw data of the sample object and generate the sample reconstructed image based on the sample raw data. Furthermore, the processing device 120 may perform feature extraction on the sample reconstructed image to obtain the first label lesion information and the second label lesion information. In some embodiments, at least a portion of the first label lesion information and the second label lesion information may be determined manually. More descriptions regarding the first label lesion information and the second label lesion information may be found in operations 320 and 330.

In some embodiments, the raw data analysis model and the image analysis model may be obtained by jointly training the first preliminary model and the second preliminary model. Training of the first preliminary model and the second preliminary model includes a plurality of iterations. In each iteration, the processing device 120 inputs the sample raw data into the first preliminary model, and the first preliminary model outputs predicted first lesion information. Subsequently, the processing device 120 compares the predicted first lesion information with the first label lesion information to determine a first loss value. Further, the processing device 120 inputs the sample reconstructed image and the predicted first lesion information into the second preliminary model, and the second preliminary model outputs predicted second lesion information. Then, the processing device 120 compares the predicted second lesion information with the second label lesion information to determine a second loss value. The processing device 120 may update the first preliminary model and the second preliminary model based on the first loss value and the second loss value.

After the plurality of iteration processes, until a termination condition for model training is satisfied, the processing device 120 may stop the model training and designate the first preliminary model and the second preliminary model obtained in the last iteration as the raw data analysis model and the image analysis model. The termination condition may include the loss function value being less than a threshold, a count of iterations meeting a requirement, or the like.

Figure 7:
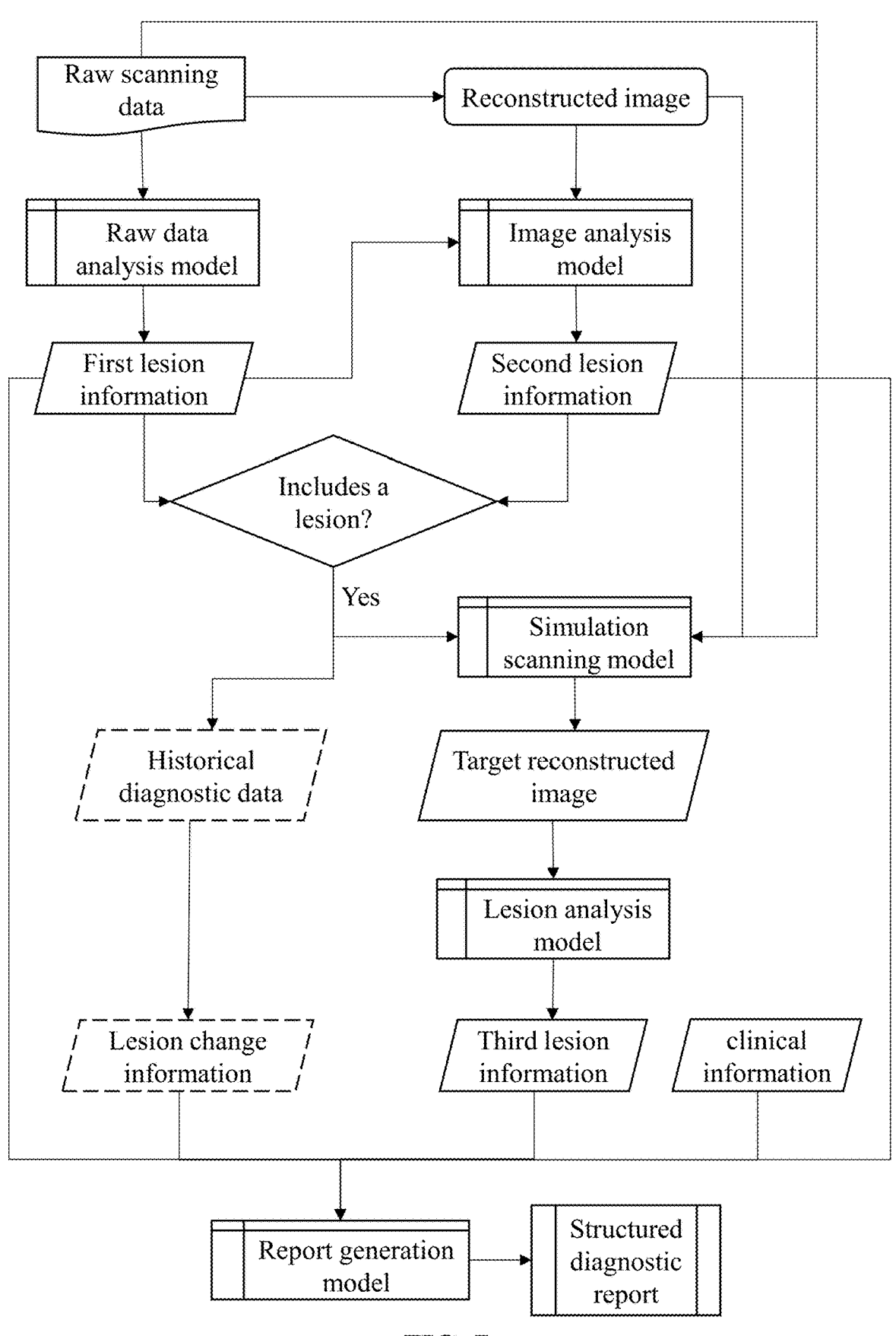
FIG. 7 is a schematic diagram illustrating an exemplary process for generating a structured diagnostic report according to some embodiments of the present disclosure.

FIG. 7 is a schematic diagram illustrating an exemplary process for generating a structured diagnostic report according to some embodiments of the present disclosure.

As shown in FIG. 7, the process for generating the structured diagnostic report includes: obtaining raw scanning data of a target object; generating a reconstructed image of the target object based on the raw scanning data; inputting the raw scanning data into a raw data analysis model, the raw data analysis model outputting first lesion information; inputting the reconstructed image and the first lesion information into an image analysis model, the image analysis model outputting second lesion information; determining whether the target object includes a lesion based on the first lesion information and the second lesion information; in response to determining that the target object includes the lesion, inputting the raw scanning data and the reconstructed image into a simulation scanning model, the simulation scanning model outputting a target reconstructed image; inputting the target reconstructed image into a lesion analysis model, the lesion analysis model outputting third lesion information; and inputting the first lesion information, the second lesion information, the third lesion information, and clinical information into a report generation model, the report generation model outputting a structured diagnostic report. In some embodiments, in response to determining that historical diagnostic data relating to the lesion exists, the process further includes: determining lesion change information based on the historical diagnostic data, the first lesion information, the second lesion information, and the third lesion information; and inputting the first lesion information, the second lesion information, the third lesion information, the clinical information, and the lesion change information into the report generation model, the report generation model outputting the structured diagnostic report.

FIG. 9 is a schematic diagram illustrating an exemplary process for generating a reference treatment plan according to some embodiments of the present disclosure. In some embodiments, the operations of process 900 are performed by the treatment prediction module. As shown in FIG. 9, the process 900 may include the following operations.

In 910, one or more reference treatment plans for the lesion may be determined based on the first lesion detection result, the second lesion detection result, the third lesion detection result, the clinical information, and the diagnostic result.

Each reference treatment plan may include a plurality of treatment plan parameters. For example, the plurality of treatment plan parameters may include a drug name, a dosage, a radiotherapy target area, a dose distribution map, or the like. In some embodiments, the treatment prediction module may, based on the first lesion detection result, the second lesion detection result, the third lesion detection result, the clinical information, and the diagnostic result, search medical treatment guidelines, knowledge graphs, etc., to obtain preset standard treatment plans as the reference treatment plans.

In some embodiments, the treatment prediction module may automatically generate the reference treatment plans based on the first lesion detection result, the second lesion detection result, the third lesion detection result, the clinical information, and the diagnostic result.

Figure 10:
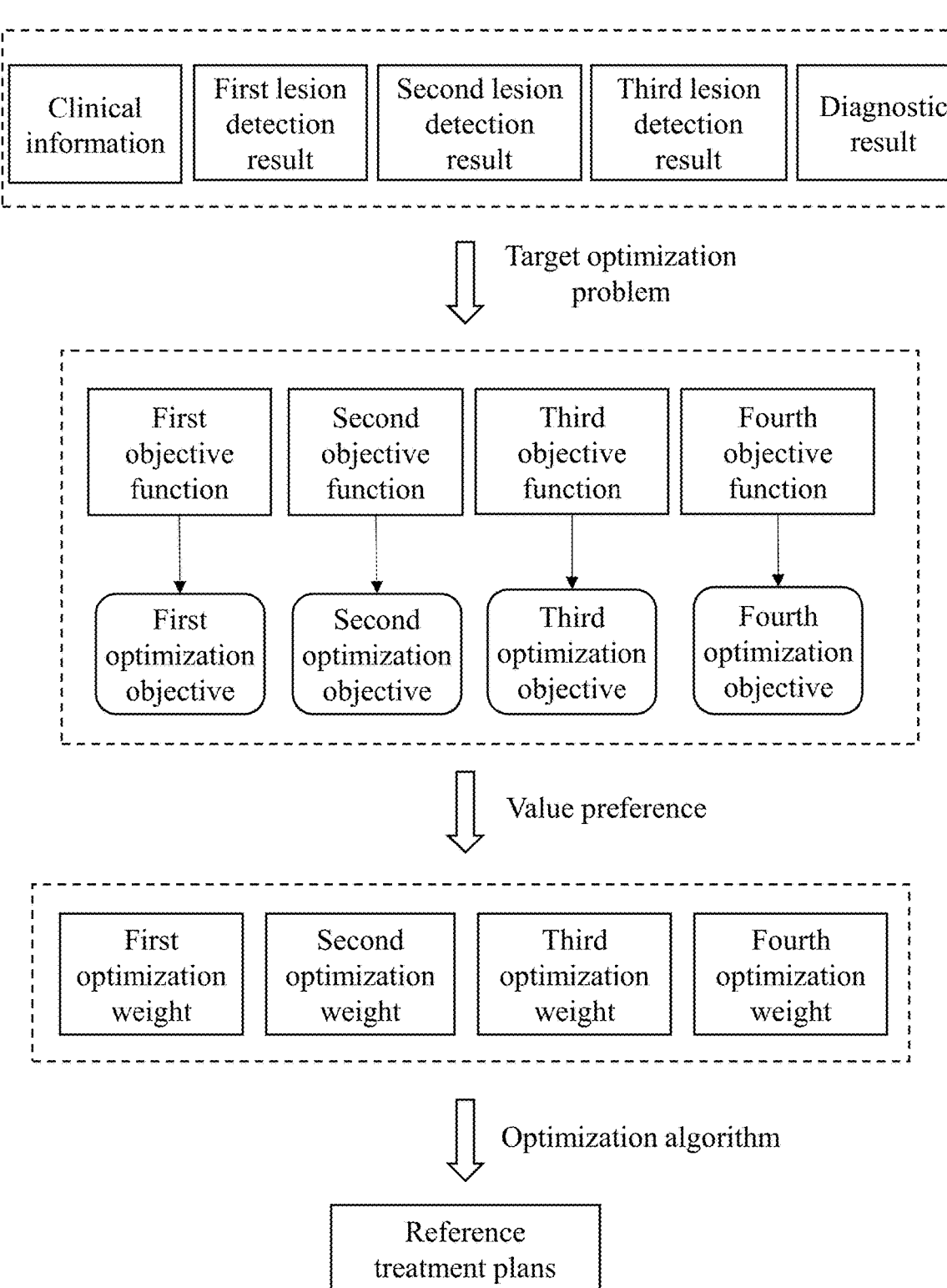
FIG. 10 is a schematic diagram illustrating an exemplary process for generating a reference treatment plan according to some embodiments of the present disclosure.

FIG. 10 is a schematic diagram illustrating an exemplary process for generating a reference treatment plan according to some embodiments of the present disclosure. As shown in FIG. 10, the treatment prediction module may construct a target optimization problem based on the first lesion detection result, the second lesion detection result, the third lesion detection result, the clinical information, and the diagnostic result. The target optimization problem includes a first optimization objective, a second optimization objective, a third optimization objective, and a fourth optimization objective. The first optimization objective is quantified by a first objective function for characterizing efficacy. The first optimization objective aims to pursue maximized treatment efficacy. The second optimization objective is quantified by a second objective function for characterizing safety. The second optimization objective aims to pursue minimized side effects. The third optimization objective is optimized by a third objective function for characterizing treatment cost. The third optimization objective aims to pursue minimized economic cost. The fourth optimization objective is quantified by a fourth objective function for characterizing compliance with treatment guidelines. The fourth optimization objective aims to pursue maximized compliance to ensure that the generated treatment plans are consistent with the recommended principles of medical treatment guidelines, safeguarding the standardization and scientific nature of the treatment.

Further, the treatment prediction module may generate the one or more reference treatment plans by solving, under a medical constraint, the target optimization problem using an optimization algorithm based on the first optimization objective, the second optimization objective, the third optimization objective, and the fourth optimization objective. The medical constraint may be provided by a medical knowledge base and transformed into rules that must be adhered to during solving the optimization algorithm. The medical constraint may include a dose safety constraint, a contraindication constraint, a physiological adaptability constraint, a treatment protocol constraint, or the like. The dose safety constraint may be set based on drug toxicology and organ tolerance data. The contraindication constraint may be set based on drug interactions, allergy history, and specific disease states. The physiological adaptability constraint may be determined based on organ function indicators of the target object. The treatment protocol constraint may be set based on clinical guidelines and medical regulations. Before optimization solving, the treatment prediction module may select one or more constraint conditions applicable to the target object from the knowledge base based on the clinical information of the target object. The optimization algorithm searches only within a feasible region satisfying all constraint conditions to ensure that the generated reference treatment plans all satisfy medical safety requirements.

In some embodiments, the treatment prediction module may generate one or more initial treatment plans based on a medical treatment guideline, a knowledge graph, or the like. For example, the aforementioned preset standard treatment plans may be used as initial treatment plans. Then, the treatment prediction module performs a plurality of iteration processes. In some embodiments, in each iteration process, for each candidate treatment plan, the treatment prediction module may determine function values for the first objective function, the second objective function, the third objective function, and the fourth objective function. If it is the first iteration process, the initial treatment plans are the candidate treatment plans. For example, for the first objective function, the treatment prediction module may input the candidate treatment plan, the first lesion detection result, the second lesion detection result, the third lesion detection result, the clinical information, and the diagnostic result into a treatment efficacy prediction unit, and use the output value of the treatment efficacy prediction unit as the function value of the first objective function. The treatment prediction module may combine the candidate treatment plan with clinical information (e.g., liver and kidney function and allergy history) and, based on a preset drug safety knowledge base and side effect prediction rules, determine a comprehensive score characterizing treatment safety risk, and use the comprehensive score as the function value of the second objective function. The treatment prediction module may query a medical cost database based on the parameters of the candidate treatment plan (e.g., a drug type, a dosage, and a course of treatment) to determine a predicted total economic cost of the candidate treatment plan, and use a value of the predicted total economic cost as a function value of the third objective function. The treatment prediction module may integrate the candidate treatment plan with diagnostic information, perform semantic matching and rule-based reasoning by leveraging treatment guidelines, knowledge graphs, etc., and determine a score that represents the degree of conformity between the candidate treatment plan and a recommended plan specified in the treatment guidelines. The score may be used as a function value of the fourth objective function. Then, based on the evaluation results of all candidate treatment plans, the treatment prediction module may use an optimization algorithm to apply operations (e.g., selection, crossover, and mutation) to generate one or more updated treatment plans, and uses the one or more updated treatment plans as candidate treatment plans for the next iteration process. The optimization algorithm may include a multi-objective evolutionary algorithm, an evolutionary algorithm, a Bayesian optimization algorithm, or the like.

In some embodiments, in each iteration process, for each candidate treatment plan, the treatment prediction module may generate an updated treatment plans based on a value preference of the target object. In some embodiments, the treatment prediction module may obtain the value preference of the target object. The value preference of the target object refers to a degree of importance the target object places on a plurality of indicators (e.g., efficacy, safety, and treatment cost). For example, the value preference may include efficacy priority, safety priority, treatment cost priority, adherence to a standard treatment guideline, or the like. Further, for each optimization objective of the first optimization objective, the second optimization objective, the third optimization objective, and the fourth optimization objective, the treatment prediction module may determine an optimization weight corresponding to the optimization objective based on the value preference. As shown in FIG. 10, the treatment prediction module may determine a first optimization weight corresponding to the first optimization objective, a second optimization weight corresponding to the second optimization objective, a third optimization weight corresponding to the third optimization objective, and a fourth optimization weight corresponding to the fourth optimization objective. In some embodiments, a sum of the first optimization weight, the second optimization weight, the third optimization weight, and the fourth optimization weight equals 1. If the value preference of the target object indicates the efficacy priority, a higher value is assigned to the first optimization weight, while lower values are assigned to the second optimization weight, the third optimization weight, and the fourth optimization weight. If the value preference indicates both the efficacy priority and the safety priority, higher values are assigned to the first optimization weight and the second optimization weight, while lower values are assigned to the third optimization weight and fourth optimization weight. If the value preference indicates the treatment cost priority, a higher value is assigned to the third optimization weight, while lower values are assigned to the first optimization weight, the second optimization weight, and the fourth optimization weight. If the value preference indicates the efficacy priority and the adherence to the standard treatment guideline, higher values are assigned to the first optimization weight and the fourth optimization weight, while lower values are assigned to the second optimization weight and the third optimization weight. Then, the treatment prediction module may generate the updated treatment plan by solving, under the medical constraint, the target optimization problem using the optimization algorithm based on the first optimization objective, the second optimization objective, the third optimization objective, the fourth optimization objective, the first optimization weight, the second optimization weight, the third optimization weight, and the fourth optimization weight. In some embodiments, the treatment prediction module may perform a weighted sum of the first objective function, the second objective function, the third objective function, and the fourth objective function according to the first optimization weight, the second optimization weight, the third optimization weight, and the fourth optimization weight to generate a comprehensive objective function. For example, the treatment prediction module may generate the comprehensive objective function according to the following formula (1), with the optimization direction being to maximize the comprehensive score:

$$F = w1 * F1 + w2 * (1 - F2) + w3 * (1 - F3) + w4 * F4, \qquad (1)$$

where $w1$, $w2$, $w3$, $w4$ are the first optimization weight, second optimization weight, third optimization weight, and fourth optimization weight, respectively; $F1$ is the first objective function value; $F2$ is the second objective function value; $F3$ is the third objective function value; $F4$ is the fourth objective function value; and $F$ is the comprehensive objective function value.

In response to determining that a preset convergence condition is satisfied (e.g., reaching a preset count of iterations), the iteration process stops, and the finally generated one or more updated treatment plans are output as the one or more reference treatment plans.

In 920, the treatment evaluation result may be generated based on the reconstructed image, the first lesion detection result, the second lesion detection result, the third lesion detection result, and the one or more reference treatment plans.

The treatment prediction module may process the reconstructed image, the first lesion detection result, the second lesion detection result, the third lesion detection result, and the reference treatment plans to output the treatment evaluation result.

In some embodiments, the treatment prediction module may include a feature extraction module, a fusion and prediction module, and an output module. The feature extraction module may include a 3D CNN encoder, a Transformer encoder, or the like. The feature extraction module may be configured to deeply extract multi-dimensional features (e.g., morphology, texture, and perfusion of the lesion) from the reconstructed image, the first lesion detection result, the second lesion detection result, and the third lesion detection result, and generate a first feature vector. The feature extraction module may be further configured to encode each reference treatment plan into a second feature vector. The fusion and prediction module may fuse the first feature vector and one or more second feature vectors. In some embodiments, the fusion and prediction module may include a neural network ordinary differential equation or a recurrent neural network module for predicting the dynamic process of the lesion changing over time under treatment stimulation. The output module may include a decoder, which decodes the features output by the fusion and prediction module to generate the treatment evaluation result.

According to some embodiments of the present disclosure, integrating the treatment evaluation result into the structured diagnostic report significantly enhances the practicality of the structured diagnostic report, provides support for physicians in formulating appropriate treatment plans, greatly increases the success rate of first-time treatments, reduces ineffective treatments, saves medical resources, and alleviates patient suffering. Moreover, this integration helps physicians and patients establish reasonable efficacy expectations, plan follow-up time points in advance, and achieve more proactive patient management.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Furthermore, the recited order of processing elements or sequences, or the use of numbers, letters, or other designations thereof, are not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

In some embodiments, numbers describing the number of ingredients and attributes are used. It should be understood that such numbers used for the description of the embodiments use the modifier "about", "approximately", or "substantially" in some examples. Unless otherwise stated, "about", "approximately", or "substantially" indicates that the number is allowed to vary by ±20%. Correspondingly, in some embodiments, the numerical parameters used in the description and claims are approximate values, and the approximate values may be changed according to the required characteristics of individual embodiments. In some embodiments, the numerical parameters should consider the prescribed effective digits and adopt the method of general digit retention. Although the numerical ranges and parameters used to confirm the breadth of the range in some embodiments of the present disclosure are approximate values, in specific embodiments, settings of such numerical values are as accurate as possible within a feasible range.

For each patent, patent application, patent application publication, or other materials cited in the present disclosure, such as articles, books, specifications, publications, documents, or the like, the entire contents of which are hereby incorporated into the present disclosure as a reference. The application history documents that are inconsistent or conflict with the content of the present disclosure are excluded, and the documents that restrict the broadest scope of the claims of the present disclosure (currently or later attached to the present disclosure) are also excluded. It should be noted that if there is any inconsistency or conflict between the description, definition, and/or use of terms in the auxiliary materials of the present disclosure and the content of the present disclosure, the description, definition, and/or use of terms in the present disclosure is subject to the present disclosure.

Finally, it should be understood that the embodiments described in the present disclosure are only used to illustrate the principles of the embodiments of the present disclosure. Other variations may also fall within the scope of the present disclosure. Therefore, as an example and not a limitation, alternative configurations of the embodiments of the present disclosure may be regarded as consistent with the teaching of the present disclosure. Accordingly, the embodiments of the present disclosure are not limited to the embodiments introduced and described in the present disclosure explicitly.

What is claimed is:

1. A method for generating a diagnostic report, comprising:

obtaining raw scanning data of a target object, a reconstructed image of the target object, and clinical information of the target object, wherein the raw scanning data is obtained by scanning the target object using a medical imaging device, and the reconstructed image is generated based on the raw scanning data;

determining, based on the raw scanning data, first lesion information of the target object;

determining, based on the reconstructed image and the first lesion information, second lesion information of the target object;

determining whether the target object includes a lesion based on the first lesion information and the second lesion information;

in response to determining that the target object includes the lesion, generating, based on the raw scanning data and the reconstructed image, a target reconstructed image of the lesion using a simulation scanning model;

obtaining third lesion information by performing feature extraction on the target reconstructed image; and generating a structured diagnostic report for the target object using a report generation model based on the first lesion information, the second lesion information, the third lesion information, and the clinical information.

2. The method of claim 1, wherein:

the first lesion information is determined by processing the raw scanning data using a raw data analysis model;

the second lesion information is determined by processing the reconstructed image and the first lesion information using an image analysis model; and the third lesion information is determined by processing the target reconstructed image using a lesion analysis model, wherein the raw data analysis model, the image analysis model, and the lesion analysis model are trained machine learning models.

3. The method of claim 2, wherein the raw data analysis model and the image analysis model are obtained by:

obtaining sample raw data, a sample reconstructed image corresponding to the sample raw data, first label lesion information corresponding to the sample reconstructed image, and second label lesion information corresponding to the sample reconstructed image;

obtaining the raw data analysis model by training a first preliminary model using the sample raw data and the first label lesion information;

determining sample first lesion information corresponding to the sample raw data based on the sample raw data and the raw data analysis model; and obtaining the image analysis model by training a second preliminary model using the sample reconstructed image, the sample first lesion information, and the second label lesion information.

4. The method of claim 1, wherein in response to determining that historical diagnostic data relating to the lesion exists, the method further comprises:

determining lesion change information based on the historical diagnostic data, the first lesion information, the second lesion information, and the third lesion information; and the generating a structured diagnostic report for the target object using a report generation model based on the first lesion information, the second lesion information, the third lesion information, and the clinical information includes:

generating the structured diagnostic report for the target object by processing the first lesion information, the second lesion information, the third lesion information, the clinical information, and the lesion change information using the report generation model.

5. The method of claim 1, wherein the simulation scanning model includes a simulation scanning module and an update module, the simulation scanning module is configured to generate an initial target reconstructed image based on the raw scanning data, the reconstructed image, the first lesion information, the second lesion information, and an initial scanning protocol parameter; and the update module is configured to generate the target reconstructed image based on the initial target reconstructed image.

6. The method of claim 5, wherein to generate the target reconstructed image based on the initial target reconstructed image, the update module is configured to:

determine whether the initial target reconstructed image satisfies a preset condition;

in response to determining that the initial target reconstructed image does not satisfy the preset condition, adjust the initial scanning protocol parameter to generate a target scanning protocol parameter; and generate the target reconstructed image based on the target scanning protocol parameter.

7. The method of claim 1, wherein the simulation scanning model is obtained by:

obtaining a plurality of third training samples and a third preliminary model, each of the plurality of third training samples including sample raw data, a sample reconstructed image, sample first lesion information, sample second lesion information, a sample scanning protocol parameter, and a reference reconstructed image; and generating the simulation scanning model by training the third preliminary model using the plurality of third training samples based on a first loss function and a second loss function, wherein during training, for each of the plurality of third training samples:

a value of the first loss function is determined based on the reference reconstructed image and a predicted target reconstructed image generated by the third preliminary model; and a value of the second loss function is determined based on predicted raw scanning data and the sample raw data, the predicted raw scanning data being determined based on the predicted target reconstructed image.

8. The method of claim 1, wherein the first lesion information includes a first lesion detection result and a first confidence map, the second lesion information includes a second lesion detection result and a second confidence map, the third lesion information includes a third lesion detection result and a third confidence map, and the generating a structured diagnostic report for the target object using a report generation model based on the first lesion information, the second lesion information, the third lesion information, and the clinical information includes:

determining a first weight corresponding to the first lesion detection result, a second weight corresponding to the second lesion detection result, and a third weight corresponding to the third lesion detection result based on the clinical information, the first confidence map, the second confidence map, and the third confidence map; and generating the structured diagnostic report for the target object by processing the first lesion detection result, the second lesion detection result, the third lesion detection result, the first weight, the second weight, and the third weight using the report generation model.

9. The method of claim 8, wherein the determining a first weight corresponding to the first lesion detection result, a second weight corresponding to the second lesion detection result, and a third weight corresponding to the third lesion detection result based on the clinical information, the first confidence map, the second confidence map, and the third confidence map includes:

determining a case type of the target object based on the clinical information;

determining a preset first weight corresponding to the first lesion detection result, a preset second weight corresponding to the second lesion detection result, and a preset third weight corresponding to the third lesion detection result based on the case type; and determining the first weight, the second weight, and the third weight by adjusting the preset first weight, the preset second weight, and the preset third weight based on the first confidence map, the second confidence map, and the third confidence map.

10. The method of claim 8, wherein the structured diagnostic report for the target object includes a diagnostic result and a traceability basis, and the traceability basis indicates information on which the diagnostic result is based.

11. The method of claim 10, wherein the report generation model includes:

a feature fusion module, configured to determine a consistency detection result, fused feature information, and an initial traceability basis corresponding to the fused feature information by performing consistency detection and feature fusion based on the first lesion detection result, the second lesion detection result, the third lesion detection result, the first weight, the second weight, the third weight, and the clinical information; and a structured report generation module, configured to:

determine the diagnostic result based on the fused feature information;

determine the traceability basis based on the initial traceability basis; and generate the structured diagnostic report based on the consistency detection result, the diagnostic result, and the traceability basis.

12. The method of claim 11, wherein the structured diagnostic report for the target object further includes a treatment evaluation result, and the report generation model further includes a treatment prediction module, the treatment prediction module is configured to:

determine one or more reference treatment plans for the lesion based on the first lesion detection result, the second lesion detection result, the third lesion detection result, the clinical information, and the diagnostic result; and generate the treatment evaluation result based on the reconstructed image, the first lesion detection result, the second lesion detection result, the third lesion detection result, the clinical information, and the one or more reference treatment plans;

the structured report generation module is further configured to generate the structured diagnostic report based on the treatment evaluation result, the consistency detection result, the diagnostic result, and the traceability basis.

13. The method of claim 12, wherein the treatment evaluation result includes, for each reference treatment plan of the one or more reference treatment plans, at least one of an efficacy prediction indicator, a predicted medical image of the lesion, a side effect assessment, and a recommendation index.

14. The method of claim 12, wherein determining one or more reference treatment plans for the lesion based on the first lesion detection result, the second lesion detection result, the third lesion detection result, the clinical information, and the diagnostic result includes:

constructing a target optimization problem based on the first lesion detection result, the second lesion detection result, the third lesion detection result, the clinical information, and the diagnostic result, the target optimization problem including a first optimization objective, a second optimization objective, a third optimization objective, and a fourth optimization objective, wherein the first optimization objective is quantified by a first objective function for characterizing efficacy, the second optimization objective is quantified by a second objective function for characterizing safety, the third optimization objective is quantified by a third objective function for characterizing treatment cost, and the fourth optimization objective is quantified by a fourth objective function for characterizing compliance with treatment guidelines; and generating the one or more reference treatment plans by solving, under a medical constraint, the target optimization problem using an optimization algorithm based on the first optimization objective, the second optimization objective, the third optimization objective, and the fourth optimization objective.

15. The method of claim 14, wherein the generating the one or more reference treatment plans by solving, under a medical constraint, the target optimization problem using an optimization algorithm based on the first optimization objective, the second optimization objective, the third optimization objective, and the fourth optimization objective includes:

obtaining a value preference of the target object;

for each optimization objective of the first optimization objective, the second optimization objective, the third optimization objective, and the fourth optimization objective, determining an optimization weight corresponding to the optimization objective based on the value preference;

generating the one or more reference treatment plans by solving, under the medical constraint, the target optimization problem using the optimization algorithm based on the first optimization objective, the second optimization objective, the third optimization objective, the fourth optimization objective, and the optimization weight corresponding to each optimization objective.

16. A system for generating a diagnostic report, comprising:

at least one storage device configured to store computer instructions; and at least one processor in communication with the at least one storage device, wherein when executing the computer instructions, the at least one processor is configured to cause the system to perform operations including:

obtain raw scanning data of a target object, a reconstructed image of the target object, and clinical information of the target object, wherein the raw scanning data is obtained by scanning the target object using a medical imaging device, and the reconstructed image is generated based on the raw scanning data;

determine, based on the raw scanning data, first lesion information of the target object;

determine, based on the reconstructed image and the first lesion information, second lesion information of the target object;

determine whether the target object includes a lesion based on the first lesion information and the second lesion information;

in response to determining that the target object includes the lesion, generate, based on the raw scanning data and the reconstructed image, a target reconstructed image of the lesion using a simulation scanning model;

obtain third lesion information by performing feature extraction on the target reconstructed image; and generate a structured diagnostic report for the target object using a report generation model based on the first lesion information, the second lesion information, the third lesion information, and the clinical information.

17. The system of claim 16, wherein the first lesion information is determined by processing the raw scanning data using a raw data analysis model;

the second lesion information is determined by processing the reconstructed image and the first lesion information using an image analysis model; and the third lesion information is determined by processing the target reconstructed image using a lesion analysis model, wherein the raw data analysis model, the image analysis model, and the lesion analysis model are trained machine learning models.

18. The system of claim 17, wherein the raw data analysis model and the image analysis model are obtained by:

obtaining sample raw data, a sample reconstructed image corresponding to the sample raw data, first label lesion information corresponding to the sample reconstructed image, and second label lesion information corresponding to the sample reconstructed image;

obtaining the raw data analysis model by training a first preliminary model using the sample raw data and the first label lesion information;

determining sample first lesion information corresponding to the sample raw data based on the sample raw data and the raw data analysis model; and obtaining the image analysis model by training a second preliminary model using the sample reconstructed image, the sample first lesion information, and the second label lesion information.

19. The system of claim 16, wherein, in response to determining that historical diagnostic data related to the lesion exists, the at least one processor is further configured to:

determine lesion change information based on the historical diagnostic data, the first lesion information, the second lesion information, and the third lesion information; and the generating a structured diagnostic report for the target object using a report generation model based on the first lesion information, the second lesion information, the third lesion information, and the clinical information includes:

generating the structured diagnostic report for the target object by processing the first lesion information, the second lesion information, the third lesion information, the clinical information, and the lesion change information using the report generation model.

20. A non-transitory computer-readable storage medium, wherein the storage medium stores at least one set of instructions, and when one or more processors of a computing device execute the at least one set of instructions, the at least one set of instructions causes the computing device to perform a method, the method comprising:

obtaining raw scanning data of a target object, a reconstructed image of the target object, and clinical information of the target object, wherein the raw scanning data is obtained by scanning the target object using a medical imaging device, and the reconstructed image is generated based on the raw scanning data;

determining, based on the raw scanning data, first lesion information of the target object;

determining, based on the reconstructed image and the first lesion information, second lesion information of the target object;

determining whether the target object includes a lesion based on the first lesion information and the second lesion information;

in response to determining that the target object includes the lesion, generating, based on the raw scanning data and the reconstructed image, a target reconstructed image of the lesion using a simulation scanning model;

obtaining third lesion information by performing feature extraction on the target reconstructed image; and generating a structured diagnostic report for the target object using a report generation model based on the first lesion information, the second lesion information, the third lesion information, and the clinical information.

\* \* \* \* \*